United States Patent
Blye et al.

(10) Patent No.: US 7,196,074 B2
(45) Date of Patent: Mar. 27, 2007

(54) METHODS OF MAKING, USING AND PHARMACEUTICAL FORMULATIONS COMPRISING 7α, 11β-DIMETHYL-17β-HYDROXYESTRA-4, 14-DIEN-3-ONE AND 17 ESTERS THEREOF

(75) Inventors: Richard P. Blye, Highland, MD (US); Hyun K. Kim, Bethesda, MD (US); Pemmaraju Narasimha Rao, San Antonio, TX (US); Carmie Kirk Acosta, San Antonio, TX (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 401 days.

(21) Appl. No.: 10/281,794

(22) Filed: Oct. 28, 2002

(65) Prior Publication Data

US 2003/0130243 A1    Jul. 10, 2003

Related U.S. Application Data

(63) Continuation of application No. PCT/US02/09886, filed on Mar. 29, 2002, which is a continuation-in-part of application No. PCT/US01/10293, filed on Mar. 30, 2001.

(60) Provisional application No. 60/194,440, filed on Apr. 4, 2000, provisional application No. 60/193,530, filed on Mar. 31, 2000.

(51) Int. Cl.
*A61K 31/56* (2006.01)
*C07J 41/00* (2006.01)

(52) U.S. Cl. ............... 514/178; 514/179; 514/182; 514/169; 514/170; 552/525; 552/539; 552/575; 552/632; 552/639; 552/641; 552/515

(58) Field of Classification Search ............... 514/167, 514/169, 170, 182, 179; 552/647
See application file for complete search history.

(56) References Cited

U.S. PATENT DOCUMENTS

| 3,577,410 A | 5/1971 | Teller et al. |
| 5,855,905 A | 1/1999 | Oettel et al. |
| 6,313,108 B1 | 11/2001 | Loozen et al. |
| 6,492,536 B2 * | 12/2002 | Bhatnagar et al. .......... 552/646 |
| 6,670,352 B2 * | 12/2003 | Cook et al. ................. 514/179 |

FOREIGN PATENT DOCUMENTS

| DE | 2119708 | 11/1971 |
| GB | 1341061 A | 12/1973 |
| GB | 1341601 | 12/1973 |
| WO | WO 99/26962 A | 6/1999 |

OTHER PUBLICATIONS

Balasubramanian et al "Recent Developments in Cancer, Etc." Annual Reports in Medicinal Chemistry, 33, 1998, Academic Press, San Diego, pp. 151-159.*

(Continued)

*Primary Examiner*—Sabiha Qazi
(74) *Attorney, Agent, or Firm*—Leydig, Voit & Mayer, Ltd.

(57) ABSTRACT

Methods of using 7α,11β-dimethyl-17β-hydroxyestra-4,14-dien-3-one (III)

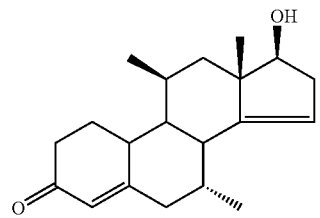

and 17 esters thereof for various hormonal therapies, oral and parenteral dosage forms comprising these actives, and processes for their preparation.

96 Claims, 22 Drawing Sheets

OTHER PUBLICATIONS

Draeua et al "Section V. Topics in Biology", Annual Reports in Medicinal Chemistfy, 31, 1996. Academic Press, San Diego, pp. 241-246.*

Nieschlag et al., "Plasma Androgen Levels in Men After Oral Administration of Testosterone or Testosterone Undecanoate," *Acta Endocrinol*, vol. 79, No. 2, pp. 366-374; 1975.

Tauber et al., "*Absolute Bioavailability of Testosterone After Oral Administration of Testosterone-Undecanoate and Testosterone,*" *European Journal of Drug Metabolism and Pharmacokinetics*, vol. 11, No. 2, pp. 145-150; 1986.

Davidson et al., "*Increasing Circulating Androgens with Oral Testosterone Undecanoate in Eugonadal Men,*" *Chemical Abstracts + Indexes American Chemical Society*, vol. 13, No. 107, p. 91; Sep. 28, 1987.

"The Merck Index, 11th Edition," *Merck & Co., Inc.*, 1989.

Monder et al., "*Studies on the Metabolism of Testosterone Trans- 4-n-butylcyclohexanoic Acid in the Cynomolgus Monkey, Macaca fascicularis,*" *Journal of Steroid Biochemistry and Molecular Biology*, vol. 50, No. 5-6, pp. 305-311; 1994.

Monder et al., "*Metabolism of Testosterone trans- 4-n-butylcyclohexyl carboxylate, a high potency androgen, in rodents and primates: in vitro studies,*" *Journal of Endocrinology*, vol. 140, No. 3, pp. 465-473; 1994.

Partsch et al., "*Injectable Testosterone Undecanoate Has More Favourable Pharmacokinetics and Pharmacodynamics than Testosterone Enanthate,*" *European Journal of Endocrinology*, vol. 132, No. 4, pp. 514-519; 1995.

"Rote Liste," *ECV Editio Cantor*, 1996.

Zitzmann et al., "Hormone Substitution in Male Hypogonadism," *Molecular and Cellular Endocrinology*, v. 161 No. 8, pp. 73-88, (Mar. 2000).

Segaloff, Albert and Gabbard, R. Bruce, "14-Dehydro-19-Nortestosterone and its 7α-methyl derivative," *Steroids* 22, 99-105 (1973).

Rasmusson, Gary H. and Arth, Glen E., "Selective Synthesis of 14-Dehydroestranes," *Steroids*, 22, 107-111 (1973).

* cited by examiner

FIG. 10 VENTRAL PROSTATE WEIGHT AND SERUM LEVELS OF CDB-1321 OR TESTOSTERONE IN CASTRATE SPRAGUE-DAWLEY RATS FOLLOWING A SINGLE SUBCUTANEOUS INJECTION OF CDB-4386A, 1321 OR 1781a IN AQUEOUS SUSPENDING VEHICLE AT THE DOSE LEVELS INDICATED (n=5)

FIG. 13 ANDROGENIC ACTIVITY OF CDB-4521A AND CDB-111C (Testosterone) IN CASTRATE SPRAGUE-DAWLEY RATS FOLLOWING SUBCUTANEOUS ADMINISTRATION IN 10%EtOH/Sesame Oil (HERSHBERGER TEST - Ventral Prostate Weight)

FIG. 14  ANDROGENIC ACTIVITY OF CDB-4521A AND CDB-110 (Methyltestosterone) FOLLOWING ORAL ADMINISTRATION IN 10% EtOH/Sesame Oil OR Aqueous Suspending Vehicle "Hershberger Test"

METHODS OF MAKING, USING AND PHARMACEUTICAL FORMULATIONS COMPRISING 7α, 11β-DIMETHYL-17β-HYDROXYESTRA-4, 14-DIEN-3-ONE AND 17 ESTERS THEREOF

RELATED APPLICATIONS

This application is a continuation of, and claims priority to, International Application No. PCT/US02/09886, filed Mar. 29, 2002, (published in English under PCT Article 21(2)) which is a continuation-in-part of, and claims priority to, International Application No. PCT/US01/10293, filed Mar. 30, 2001 (published in English under PCT Article 21(2)), and claims priority to U.S. Provisional Patent Application Nos. 60/193,530, filed Mar. 31, 2000, and 60/194,440, filed Apr. 4, 2000, each of which is incorporated by reference.

FIELD OF THE INVENTION

The present invention generally relates to methods of making and using androgenic steriods and esters of androgenic steroids.

BACKGROUND OF THE INVENTION

Androgen is a term used to identify the human male sex hormones. These hormones, which are chemically classified as steroids, are produced in the body by the testis, the cortex of the adrenal gland and, to a much lesser extent, by the ovaries. Testosterone is perhaps the most widely recognized androgen, and is responsible for the development of male characteristics in a human, including secondary sexual characteristics, libido and the ability to produce sperm.

When a person is unable to synthesize testosterone, therapy directed at replacing the missing hormone is commonly undertaken. In practice, however, this therapy can be problematic. For example, testosterone exhibits only weak activity when administered orally. While parenteral administration is possible, it is impractical because testosterone remains active in the body for only a short time. Research has therefore focused on identifying so-called synthetic androgens that are acceptable substitutes for natural testosterone.

A number of oral and injectable synthetic androgens have been developed over the years, including esters of various androgens. While these esters are hydrolyzed in the body into their corresponding biologically-active alcohols, they are nonetheless administered because they slow the rapid degradation of the synthetic androgen by the body. This maximizes the amount of the biologically active alcohol that reaches the bloodstream.

Unfortunately, the activity of these androgen esters is unpredictable. Different androgens sharing the same ester group exhibit varying and unpredictable levels of activity, as do androgens having the same basic chemical structure, but different ester groups.

One of the esters that has emerged as a viable injectable synthetic androgen is testosterone enanthate. This enanthate is presently used extensively via intramuscular (IM) injection for hormone replacement therapy in hypogonadal men, and as the androgenic component of several experimental male contraceptives. One drawback of this active is that it is not exceptionally long-acting—it must be administered IM every two weeks to maintain testosterone levels within a normal (therapeutic) range in hypogonadal men.

More specifically, testosterone enanthate is presently administered IM for the treatment of hypogonadism at a dose of 200 mg every two or three weeks. If this enanthate is used for male contraception, it may be administered parenterally at from about 200–400 mg every week, and if used as the androgenic component with estrogen or progestins for contraception, it may be administered at about 200 mg every two weeks. Testosterone bucyclate is another synthetic androgen disclosed in, e.g., U.S. Pat. No. 4,948,790. If administered parenterally for the treatment of hypogonadism, this bucyclate would require a dose of about 1200 mg (given as 3 injections of 1 ml each due to its solubility) to retain activity for about 2–3 months.

The development of androgens that exhibit activity after oral administration has been less successful. At present, the most widely used effective oral formulation includes methyltestosterone as the active ingredient, administered at 10–50 mg methyltestosterone/day. However, this active cannot be administered on a long-term basis, as is required in androgen replacement therapy, because of its associated liver toxicity. It is well known that androgens alkylated at the $C_{17}$ position, such as methyltestosterone, exhibit such toxicity. While removal of the $C_{17}$ alkyl group may appear at first glance to be an obvious solution to this problem, alkylation at this position is believed to be necessary to prevent degradation of the active by the liver after oral administration.

Illustrative of the development efforts relating to synthetic androgens is U.S. Pat. No. 5,952,319. While this patent identifies a number of potentially-active synthetic androgens, including 7α,11β-dimethyl-17β-hydroxy-4-estren-3-one 17β-trans-4-n-butylcyclohexane carboxylate (referred to herein as 7α,11β-dimethyl-17β-hydroxy-4-estren-3-one bucyclate), it provides no data regarding the biological activity of 7α,11β-dimethyl-17β-hydroxy-4-estren-3-one bucyclate. There is similarly no data available concerning the biological activity of another synthetic androgen, 7α,11β-dimethyl-17β-hydroxyestr-4-en-3-one 17-undecanoate.

A need therefore exists for a means of overcoming the foregoing and other problems associated with androgen replacement and other therapies that require the administration of androgens.

BRIEF SUMMARY OF THE INVENTION

The present invention meets the aforesaid and other needs by providing, in one aspect, a method for providing hormonal therapy to a patient comprising the oral administration of an amount sufficient to provide such therapy (advantageously from about 1 mg/day to about 25 mg/day) of 7α,11β-dimethyl-17β-hydroxy-4-estren-3-one bucyclate, 7α,11β-dimethyl-17β-hydroxyestr-4-en-3-one 17-undecanoate, or a mixture thereof, to a patient in need thereof.

A related aspect of the present invention contemplates providing hormonal therapy to a patient comprising the oral administration of an androgen selected from the group consisting of 7α,11β-dimethyl-17β-hydroxyestra-4,14-dien-3-one, 17 esters of 7α,11 β-dimethyl-17β-hydroxyestra-4,14-dien-3-one, or mixtures thereof in an amount effective to provide hormonal therapy to a patient in need thereof.

The foregoing aspects of the invention are predicated in significant part on the unexpected discoveries that 7α,11β-dimethyl-17β-hydroxy-4-estren-3-one bucyclate (also referred to herein as "the bucyclate"), 7α,11β-dimethyl-17β-hydroxyestr-4-en-3-one 17-undecanoate (also referred to herein as "the undecanoate"), 7α,11β-dimethyl-17β-hydroxyestra-4,14-dien-3-one (also referred to herein as "14-dehydromethandrolone"), and 17 esters of 7α,11β-dimethyl-17β-hydroxyestra-4,14-dien-3-one (also referred to herein as "17 esters of 14-dehydromethandrolone"), do not degrade after oral administration even though each lacks an alkyl group at the $C_{17}$ position, and exhibit activity far in excess of the current oral standard, methyltestosterone. These surprising discoveries permit hormonal therapies requiring the administration of an androgen to be conducted utilizing oral dosages of the foregoing androgens that are significantly lower than those required when administering oral methyltestosterone to effect the same therapy. A further expected benefit of using these compounds is that liver toxicity, if any, should be minimal because these compounds are not alkylated at the $C_{17}$ position.

In another aspect, the present invention comprises a method for providing hormonal treatment comprising the parenteral administration of an effective amount, advantageously from about 1 mg up to about 100 mg of the bucyclate and/or the undecanoate at intervals of at least about two weeks, and preferably up to about 600 mg at much longer intervals, e.g., a single administration of 600 mg providing effective therapy for up to about three months.

A related aspect contemplates a method for providing hormonal treatment comprising administering parenterally an androgen selected from the group consisting of 7α,11β-dimethyl-17β-hydroxyestra-4,14-dien-3-one, 17 esters of 7α,11β-dimethyl-17β-hydroxyestra-4,14-dien-3-one, or mixtures thereof in an amount effective to provide hormonal therapy to a patient in need thereof.

The aspects of the invention are predicated in part on the surprising relatively high potency, and unexpected long-term activity, of the bucyclate and undecanoate when administered parenterally, which potency is higher and activity longer-lasting than esters of other potent androgenic steroids, even bucyclic esters thereof. This activity was unexpected in view of the preparation and evaluation of several bucyclic esters of potent androgenic steroids other than 7α,11β-dimethyl-17β-hydroxy-4-estren-3-one bucyclate, the former group of esters yielding disappointing results.

Another aspect of the present invention includes separate processes for preparing the bucyclate, undecanoate, 14-dehydrodimethandrolone and 17 esters of 14-dehydrodimethandrolone which provide these actives in relatively high yield, and advantageously in a solid form, preferably crystalline, at room temperature. As each can be produced in solid form, the preparation of aqueous microcrystalline suspensions for parenteral administration (with the exception of the 17 undecanoate ester of 14-dehydrodimethandrolone which would not crystallize) is possible. Moreover, because these actives are solid at room temperature, one is able to control the average particle size and particle size distribution of the solids, thereby positively affecting the duration of activity after parenteral administration of the respective suspensions.

Related aspects of the present invention include certain intermediates, in amorphous or, preferably, crystalline form, as well as one or more steps used in the aforementioned preferred process for preparing the bucyclate, undecanoate, 14-dehydrodimethandrolone and 17 esters of 14-dehydrodimethandrolone.

Further aspects of the present invention include various formulations of these actives, including tablets, caplets, extended release tablets, soft gelcaps containing the actives in an oily carrier, transdermal patches, pre-filled syringes, vials and the like, in which the amount of the active(s) included therein may be determined in view of their unexpected relatively high potency and long-term activity.

It is contemplated that the hormonal therapy of the present invention includes, but is not limited to, hormone replacement therapy in males and females, male contraception, and the treatment of certain cancers, such as breast cancer.

These and other aspects and features of the present invention may best be understood with reference to the accompanying figures and in the following description of the preferred embodiments.

The various aspects of the present invention described in the following paragraphs are set forth with an emphasis on preferred embodiments. However, it will be obvious to those of ordinary skill in the art that variations of the preferred embodiments may be successfully used, and that it is intended that the invention may be practiced otherwise than as specifically described herein. The inventive methods, processes and formulations should therefore not be construed as being limited to the preferred embodiments described herein.

DETAILED DESCRIPTION OF THE PREFERRED EMBODIMENTS

The present invention provides a variety of methods for providing hormonal therapy to a patient (male or female) in need thereof. Each method requires the administration of particular actives, 7α,11β-dimethyl-17β-hydroxy-4-estren-3-one bucyclate, 7α,11β-dimethyl-17β-hydroxyestr-4-en-3-one 17-undecanoate, 7α,11β-dimethyl-17β-hydroxyestra-4,14-dien-3-one, and 17 esters of 7α,11β-dimethyl-17β-hydroxyestra-4,14-dien-3-one, either in combination or, preferably, alone. The chemical structures of certain of the actives are set forth in FIGS. 1, 12 and 17–19.

Figure 1:
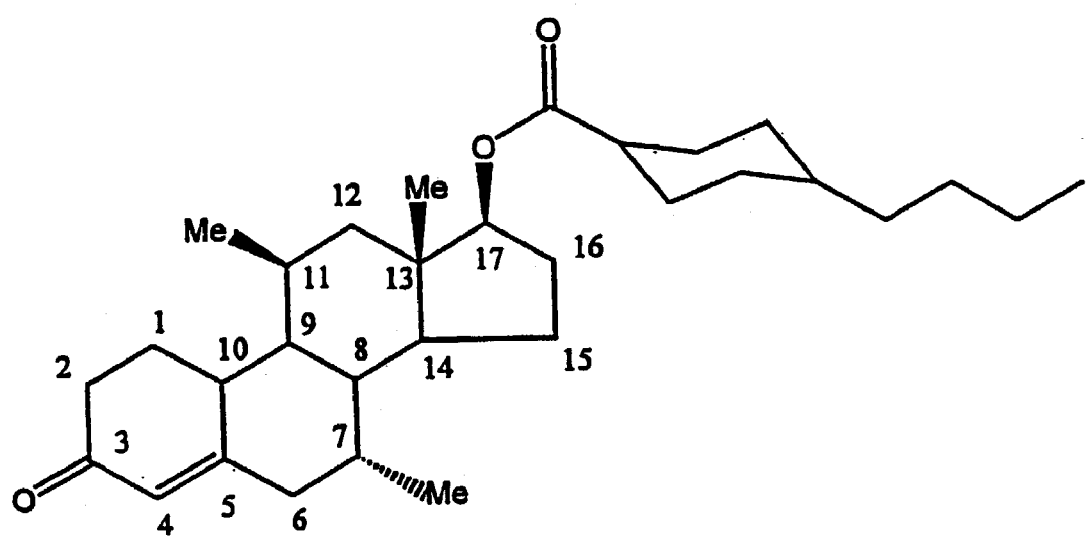
FIG. 1 illustrates the chemical structure of 7α,11β-dimethyl-17β-hydroxy-4-estren-3-one bucyclate, with numerals identifying the various carbon atom positions, including the non-alkylated $C_{17}$ position.
Figure 2A:
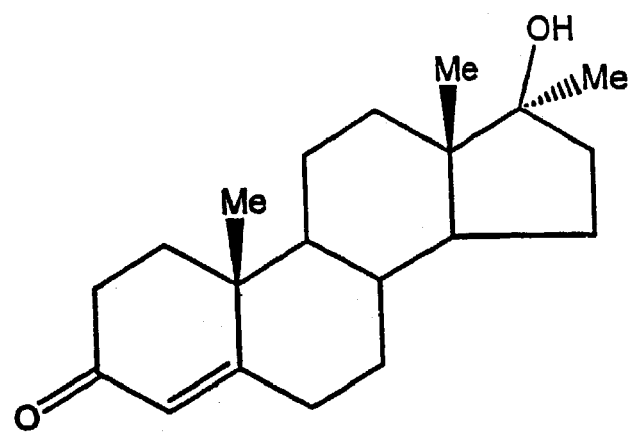
FIG. 2A illustrates the chemical structure of methyltestosterone.
Figure 2B:
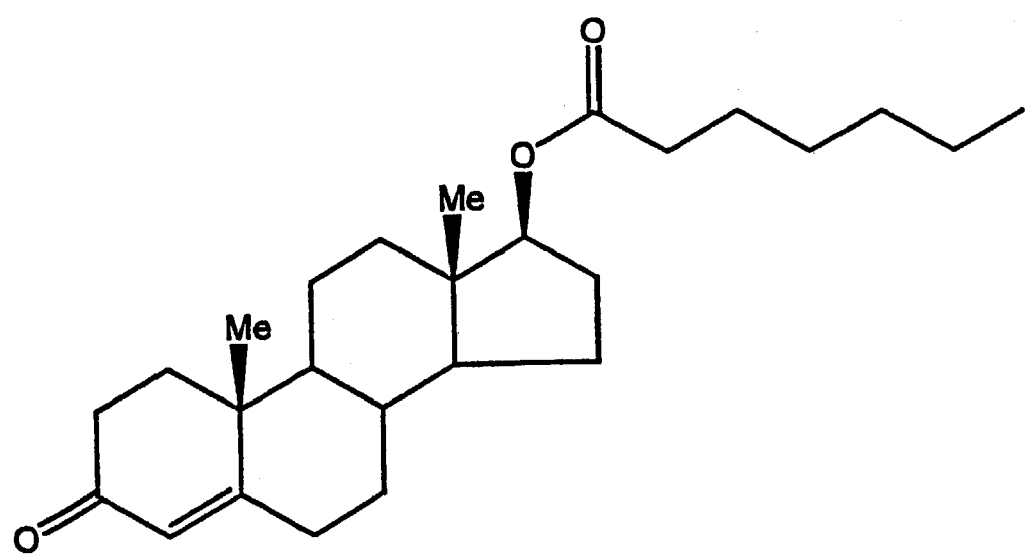
FIG. 2B illustrates the chemical structure of testosterone enanthate.

In significant part, the present invention rests upon the discovery that 7α,11β-dimethyl-17β-hydroxy-4-estren-3-one bucyclate, 7α,11β-dimethyl-17β-hydroxyestr-4-en-3-one 17-undecanoate, 7α,11β-dimethyl-17β-hydroxyestra-4,14-dien-3-one, and 17 esters of 7α,11β-dimethyl-17β-hydroxyestra-4,14-dien-3-one (also referred to herein as "actives" or "the actives"), exhibit surprising and unexpected properties in vivo. These properties permit these actives to be administered either orally or parenterally, in relatively lower amounts, at longer time intervals, (at least with respect to those activities that can provide as a solid), and with less side effects, as compared to existing alternative synthetic androgens, e.g., methyltestosterone, testosterone enanthate. The chemical structures of these two well-known compounds (methyltestosterone, testosterone enanthate) are set forth in FIGS. 2A and 2B, respectively.

The surprising properties of 7α,11β-dimethyl-17β-hydroxy-4-estren-3-one bucyclate, 7α,11β-dimethyl-17β-hydroxyestr-4-en-3-one 17-undecanoate, 7α,11β-dimethyl-17β-hydroxyestra-4,14-dien-3-one, and 17 esters of 7α,11β-dimethyl-17β-hydroxyestra-4,14-dien-3-one, render these actives well suited for any hormonal therapy in which an androgen is required, or desired. By way of example only, and without intending to limit the therapeutic uses of the actives, the actives may be used in the treatment of hypogonadal males, e.g., hypogonadatropic eunuchoidism (complete, incomplete, delayed puberty), fertile eunuch, prepubertal panhypopituitarism, postpubertal pituitary failure (selective, panhypopituitarism). The actives may also be administered (either alone or, more effectively, in combination with one or more steroidal progestins or estrogens) to induce and maintain fertility suppression in male animals, or as an androgenic component for feedback. Further, and due to their anabolic properties, the actives may be administered to promote and maintain muscle growth and maintenance. These properties can be particularly important in persons afflicted with muscle wasting diseases such as AIDS, but are more generally applicable to the elderly who typically have relatively low muscle mass. In addition, the actives may be used for the treatment of cancer, e.g., the pilliative treatment of breast cancer in men and women, the treatment of osteoporosis, anemia, anabolism, hormonal replacement therapy (in males and females) and hypergonadotropic conditions (e.g., Klinefelter's, Reifenstein's, functional prepubertal castration syndrome, male Turner's syndrome, serotoli cell-only syndrome, adult seminiferous tubule failure (e.g., mumps orchitis, irradiation, idiopathic, myotonia dystrophica), adult Leydig cell failure).

The unexpected properties of 7α,11β-dimethyl-17β-hydroxy-4-estren-3 -one bucyclate, 7α,11β-dimethyl-17β-hydroxyestr-4-en-3 -one 17-undecanoate, 7α,11β-dimethyl-17β-hydroxyestra-4,14-dien-3-one, and 17 esters of 7α,11β-dimethyl-17β-hydroxyestra-4,14-dien-3-one, were discovered after a series of in vivo animal studies undertaken in Sprague-Dawley rats. For example, based upon these experiments, it was unexpectedly found that the foregoing activities, despite their lack of alkylation at the $C_{17}$ position, not only do not degrade after oral administration, but exhibit activity far in excess of the current oral standard, methyltestosterone. Moreover, this lack of alkylation is expected to minimize, or eliminate, any attendant liver toxicity. Thus, the foregoing and other therapies may be conducted utilizing dosages of the actives that are significantly lower than those expected, and less than that required when administering methyltestosterone, to effect the same therapy. This is accomplished without the attendant concern of liver toxicity associated with existing synthetic androgens.

More specifically, it was found that the oral activity of 7α,11β-dimethyl-17β-hydroxy-4-estren-3-one bucyclate was about four times greater than methyltestosterone (thereby providing what may be referred to as a potentcy ratio of about 4 relative to the standard, in this case, methyltestosterone). The oral activity of the undecanoate, 7α,11β-dimethyl-17β-hydroxyestr-4-en-3-one 17-undecanoate, was found to be about twice that of methyltestosterone. With regard to certain of the other actives, the oral activity of 7α,11β-dimethyl-17β-hydroxyestra-4,14 -dien-3-one was found to be about twice (1.96), 7α,11β-dimethyl-17β-hydroxyestra-4,14-dien-3-one 17-undecanoate was found to be at least about twice, 7α,11β-dimethyl-17β-hydroxyestra-4,14-dien-3-one 17β-4-n-butylcyclohexanecarboxylate was found to be at least about six times, relative to the activity of methyltestosterone. Moreover, and with respect to both the bucyclate and undecanoate, it was found that this oral activity was maximized when the actives were formulated with an oily carrier. Unexpectedly high levels of activity were also discovered in connection with the parenteral administration of the actives. In contrast to the oral formulation, activity was maximized when the parenteral formulation comprised the actives in an aqueous carrier.

As a general statement, it was found that the effective oral dosage of any of the actives for any hormone replacement therapy which requires an androgen, e.g., the treatment of hypogonadism, will be the inverse of its potency ratio relative to the amount of the standard required to provide the same effect, e.g., the amount of methyltestosterone administered orally required to provide the same effect.

For example, and in the case of hypogonadism, 7α,11β-dimethyl-17β-hydroxy-4-estren-3-one bucyclate may be orally administered in therapeutically effective amounts. More specifically, the oral dosage may range from about 1 mg/day to about 25 mg/day, advantageously from about 2 mg/day to about 20 mg/day, and preferably up to about 15 mg/day. Administration of the undecanoate to effect this therapy may be undertaken within the foregoing bucyclate therapeutic dosage ranges, but is preferably undertaken at relatively greater levels relative to that of the bucyclate due to the undecanoate's slightly lower oral activity. For example, the undecanoate may be administered at from about 1 mg/day to about 75 mg/day, advantageously from about 2 mg/day to about 50 mg/day, and preferably up to about 25 mg/day.

More generally, the actives, including the 17-undecanoate, may be administered at an average dosage of from about 1 mg to about 50 mg per day, and advantageously from about 5 mg to about 40 mg per day. The average daily dosage of the relatively potent actives may range from about 1 mg to about 25 mg.

The oral dosage regimens described herein, set forth on the basis of milligrams/day, includes any dosage regimen that is able to provide that dosage level to a patient per day. For example, an extended release formulation of an active may not need to be administered each day, yet would provide the required daily dosage. However, administration of the therapeutic dosage on a daily basis is the preferred method of treatment.

The effective oral dosage of the actives, for example, the bucyclate, the 17β-4-n-butylcyclohexanecarboxylate ester of 7α,11β-dimethyl-17β-hydroxyestra-4,14-dien-3-one for the treatment of cancer, e.g., breast cancer in women, can vary, but will range from at least about 10 mg/day, advantageously at least about 25 mg/day, and preferably at least about 50 mg/day. Administration of the undecanoate or the 17 undecanoate ester of 7α,11β-dimethyl-17β-hydroxyestra-4,14-dien-3-one to effect this therapy may, as before, be undertaken within the foregoing bucyclate therapeutic dosage ranges, but is preferably undertaken at relatively greater levels relative to that of the bucyclate. For example, the undecanoate may be administered in an amount of at least about 20 mg/day, advantageously at least about 50 mg/day, and preferably at least about 100 mg/day.

In the use of the actives for male contraception, amounts effective to provide such therapy may be administered. Generally, the effective oral doses may vary, but can range from about 1 to about 50 mg per day. Of course, the greater the relative potency, the lesser the dose. For example, for 7α,11β-dimethyl-17β-hydroxy-4-estren-3-one bucyclate and the 17β-4-n-butylcyclohexanecarboxylate esters of 7α,11β-dimethyl-17β-hydroxyestra-4,14-dien-3-one, when administered for male contraception, an effective oral dose may range from about 1 mg/day to about 25 mg/day, advantageously from about 2 mg/day to about 20 mg/day, and up to about 15 mg/day. Administration of the undecanoate and the 17 undecanoate ester to effect this therapy may, as before, be undertaken within the foregoing bucyclate therapeutic dosage ranges, but is preferably undertaken at relatively greater levels relative to that of the bucyclate. For example, these actives may be administered in an amount ranging from about 1 mg/day to about 50 mg/day, advantageously from about 2 mg/day to about 40 mg/day, and up to about 30 mg/day.

In the case of conditions requiring chronic hormonal therapy, such as hypogonadism, an injectable bucyclate, undecanoate, 7α,11β-dimethyl-17β-hydroxyestra-4,14-dien-3-one, and/or 17 esters of 7α,11β-dimethyl-17β-hydroxyestra-4,14-dien-3-one formulation is preferably administered. This preference is based upon the unexpected discovery that these actives are surprisingly potent and long-acting when dispersed (preferably as a suspension) in an aqueous formulation (with the exception of the 17 undecanoate ester of 7α,11β-dimethyl-17β-hydroxyestra-4,14-dien-3-one, which exhibit relatively high potency and thus may be parenterally administered for any hormonal therapy, but are not long-acting relative to other actives provided herein). Given these properties, and by way of example, the bucylate and undecanoate may be administered in an aqueous formulation at lower doses compared to both testosterone enanthate (in an oily carrier) and testosterone bucyclate, and at relatively long intervals. More specifically, and by further way of comparative example, doses of the bucyclate and undecanoate, when dispersed in an aqueous formulation, may generally range from about one-third to about three-quarters the dose of testosterone enanthate (provided in a sesame oil carrier) required to provide substantially equivalent therapeutic results, with between about one-half and about two-thirds of that latter dose being preferred. With respect to testosterone enanthate, the bucyclate, undecanoate, when dispersed in an aqueous carrier, may be administered at between about one-quarter and about one-half of the dose of testosterone enanthate to provide substantially equivalent therapeutic effects. With respect to testosterone bucyclate, the crystalline 17 esters of 7α,11β-dimethyl-17β-hydroxyestra-4,14-dien-3-one (e.g., the 17β-4-n-butylcyclohexanecarboxylate ester thereof), when dispersed in an aqueous carrier, may be administered at between about one-quarter and about one-half of the dose of testosterone bucyclate in the same aqueous carrier to provide substantially equivalent therapeutic effects. However, if any of the actives are formulated in a non-aqueous carrier, e.g., an oily carrier comprised of sesame or other vegetable oils, it was discovered that its potency over long periods remained, but that it was substantially equivalent to that of testosterone enanthate in a sesame oil carrier.

Because of its long-acting androgenic activity, particularly when administered parenterally in an aqueous carrier in effective amounts, the bucyclate, undecanoate, 7α,11β-dimethyl-17β-hydroxyestra-4,14-dien-3-one and the crystalline 17 esters thereof (e.g., the 17β-4-n-butylcyclohexanecarboxylate ester thereof), may be administered at intervals equal to, or in excess of, about two weeks. More specifically, they may be administered at intervals of about one month, preferably about two months, more preferably once about every three months or about every two to four months. This provides a significant advantage to a patient relative to existing regimens that require therapeutic injections on a more frequent basis.

Again, the dosage of any of the actives administered parenterally (particularly those able to be administered in an aqueous formulation) in an aqueous formulation at any interval will be significantly less than the amount of testosterone enanthate used to achieve substantially similar therapeutic results. For example, in treating hypogonadism, those actives may be formulated in an aqueous carrier and provide therapeutic benefits over an extended time period may be administered in amounts ranging from about 1 mg up to about 100 mg about every two weeks, and advantageously from about 25 to about 75 mg during that period; up to about 200 mg about every month, and advantageously from 50 mg to about 150 mg during that time period; up to about 400 mg about every 2 months, and advantageously from about 100 to about 300 mg during that time period; and up to about 600 mg about every 3 months, and advantageously from about 150 mg to about 450 mg during that time period. These dosages, advantageously provided by a single injection at the beginning of each time period, are less than the dosages of testosterone enanthate and testosterone bucyclate that may be used to provide similar therapeutic effects over the same periods.

By way of further example, dosages of the bucyclate, undecanoate, 7α,11β-dimethyl-17β-hydroxyestra-4,14-dien-3-one and crystalline 17 esters thereof effective for male contraception via parenteral administration, if used alone, may range from about 25 mg/week up to about 200 mg/week, advantageously up to about 150 mg/week, and preferably from about 50 mg/week to about 100 mg/week. If used in a more typical manner, i.e., combined with estrogen and/or progestins, parenteral dosages of the foregoing actives may range from about 1 mg up to about 100 mg every about two weeks, advantageously from about 2 mg up to about 75 mg, and preferably up to about 50 mg, every two weeks. Of course, because of the long-acting activity of these actives, these dosages may be administered on a substantially linear basis if activity beyond the periods set forth above is desired.

The enhanced potency of the bucyclate, undecanoate, 7α,11β-dimethyl-17β-hydroxyestra-4,14-dien-3-one and crystalline 17 esters thereof actives advantageously permits a further advantage in that effective amounts may be administered via a single injection, which is desirable from a patient comfort and cost perspective. Equivalent therapeutic results using testosterone enanthate would require multiple injections. Of course, multiple injections of relatively lower doses of the inventive actives may be administered if required or desired. For example, actives formulated into an oily carrier, despite relatively high potency, need to be administered more frequently to obtain the desired therapy, with the dose being adjusted based upon the particular active's potency in that carrier.

While the actives may be administered alone in the treatment of cancer, it is preferably administered in coordination with one or more anti-cancer agents, e.g., therapeutically-effective amounts of chemotherapeutic agents, such as, cisplatin, carboplatin, doxorubicin, paclitaxel, taxotere, methotrexate, fluorouracil, camptothecin, cyclophosphamide and mixtures thereof, as well as therapeutically-effective amounts of anti-angiogenesis agents, either alone or in combination. The identity of suitable anti-tumor and anti-angiogenesis agents and associated dosage regimens are well known, and as such will not be repeated herein. The timing of administration of the foregoing agents may occur at any time so long as the administration does not interfere with the inventive therapeutic methods.

While the actives may be prepared using any suitable process, a further aspect of the present invention is the discovery of the preferred synthesis routes described below, which provide these actives in relatively high yield, and in solid form, preferably in crystalline form, at room temperature. The preparation of these actives in solid form at room temperature was significant, as it led to the further discovery that the long-acting effect of these actives are enhanced when included in an injectable formulation at an average particle diameter of from about 1–50 μm, and preferably from about 3–30 μm. The average particle diameter of the actives, and particularly the crystalline actives, when formulated as an injectable is thus preferably within the foregoing ranges.

As a solid at room temperature, the actives stand in marked contrast to testosterone enanthate. The latter exists as a liquid at room temperature, adversely affecting its activity over long periods of time. Further, the enanthate is precluded from commercialization as a lyophilizate or powder for reconstitution, or as a tablet, caplet or other solid dosage form.

Figure 11:
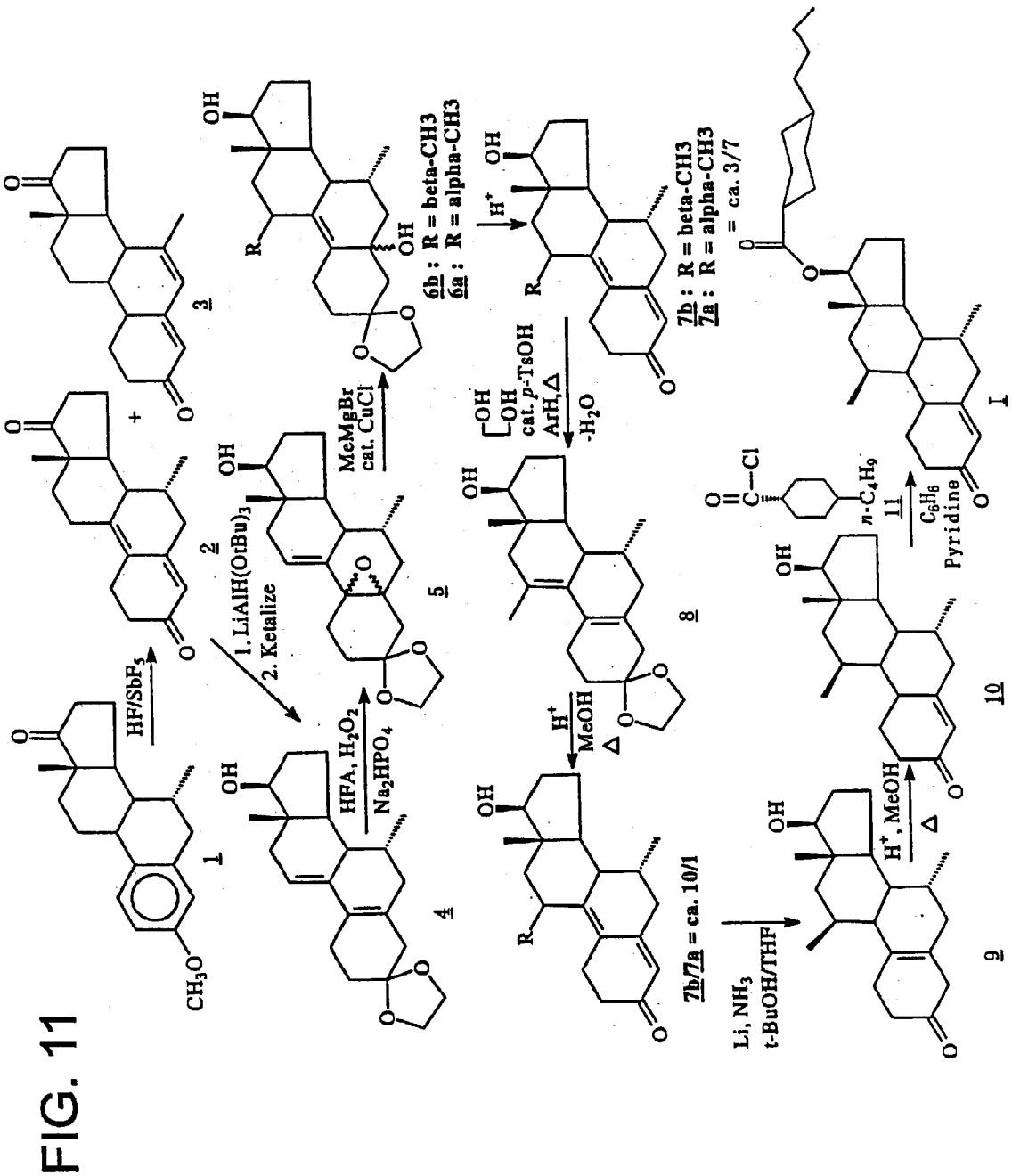
FIG. 11 is a description of a preferred method for preparing 7α,11β-dimethyl-17β-hydroxy-4-estren-3-one bucyclate.
Figure 12:
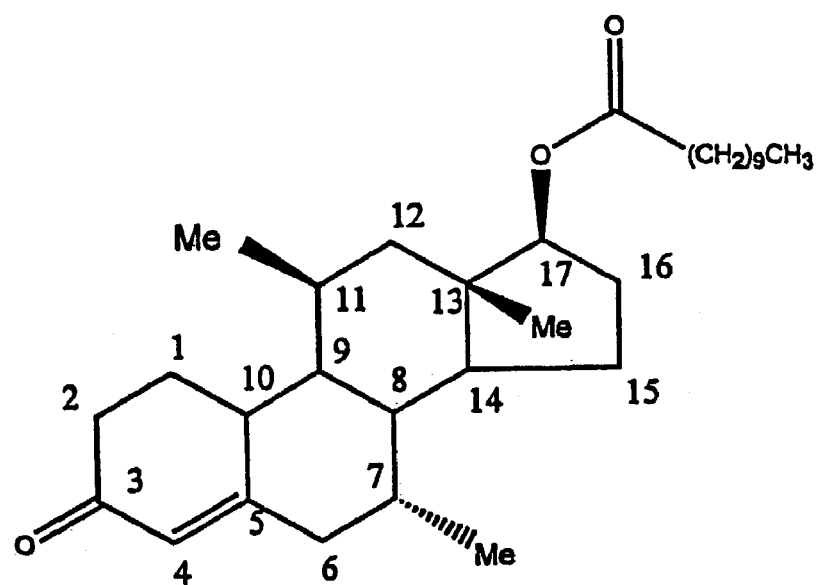
FIG. 12 illustrates the chemical structure of 7α,11β-dimethyl-17β-hydroxyestr-4-en-3-one 17-undecanoate, with numerals identifying the various carbon atom positions, including the non-alkylated $C_{17}$ position.

Turning to FIG. 11, the preferred synthesis of 7α,11β-dimethyl-17β-hydroxy-4-estren-3-one bucyclate is depicted. Generally, this synthesis comprises the steps of:

(a) converting the ether group of Compound 1

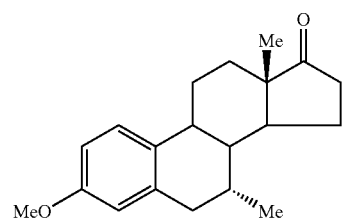

to a carbonyl group, providing Compound 2

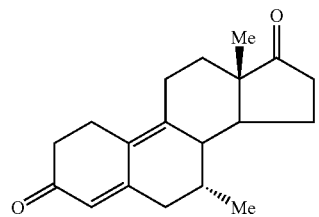

(b) ketalizing the carbonyl group of Compound 2 to provide Compound 4

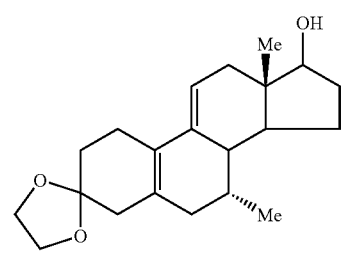

(c) epoxidizing Compound 4 to provide the epoxide of Compound 5

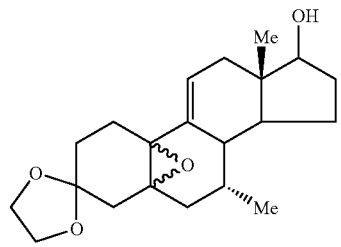

5

(d) opening the epoxide ring in Compound 5 and substituting an alkyl group at $C_{11}$ to provide Compound 6 (comprising a mixture of 11α- and 11β-methyl isomers, Compounds 6a and 6b, respectively) by use of a Grignard reagent

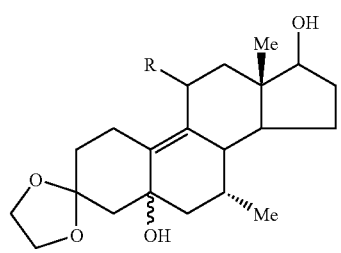

6

6a: R=alpha-Me
6b: R=beta-Me (e) deketalizing and dehydrating Compound 6 to provide Compound 7 (comprising a mixture of 11α- and 11β-methyl isomers, Compounds 7a and 7b, respectively)

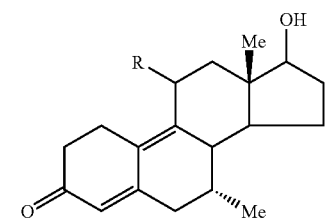

7

7a: R=alpha-Me
7b: R=beta-Me (f) converting Compound 7a to Compound 9

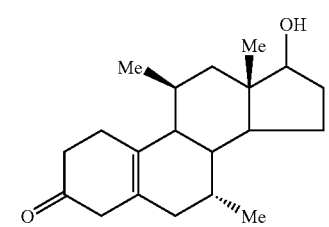

9

(g) converting Compound 9 to Compound 10

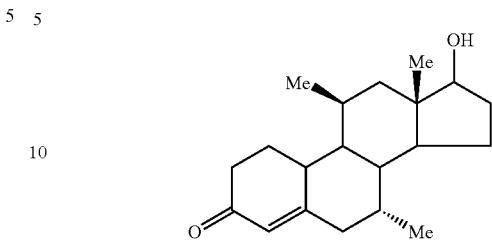

10 and (h) esterifying Compound 10 to provide Compound I (7α,11β-dimethyl-17β-hydroxy-4-estren-3-one bucyclate).

Step (a) may also yield an undesirable by-product, Compound 3

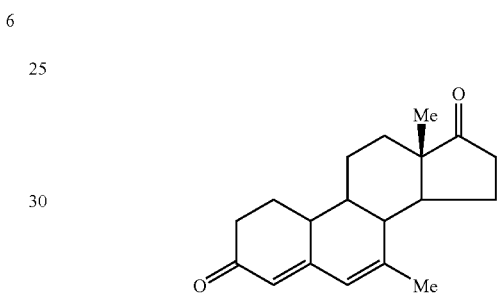

3

If desired, before step (f), one may ketalize the 11α- and 11β-methyl isomers of Compound 7 to provide Compound 8

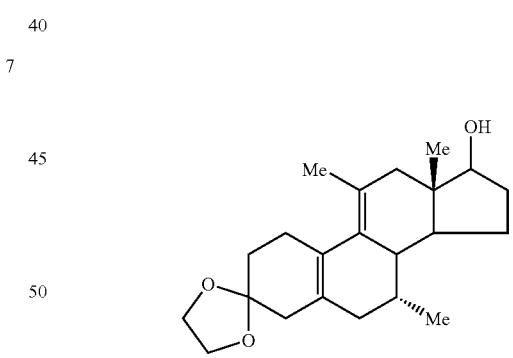

8 and then deketalize and epimerize Compound 8, thereby enhancing the ratio of the desirable 11α-methyl isomer to 11β-methyl isomer.

Figure 16:
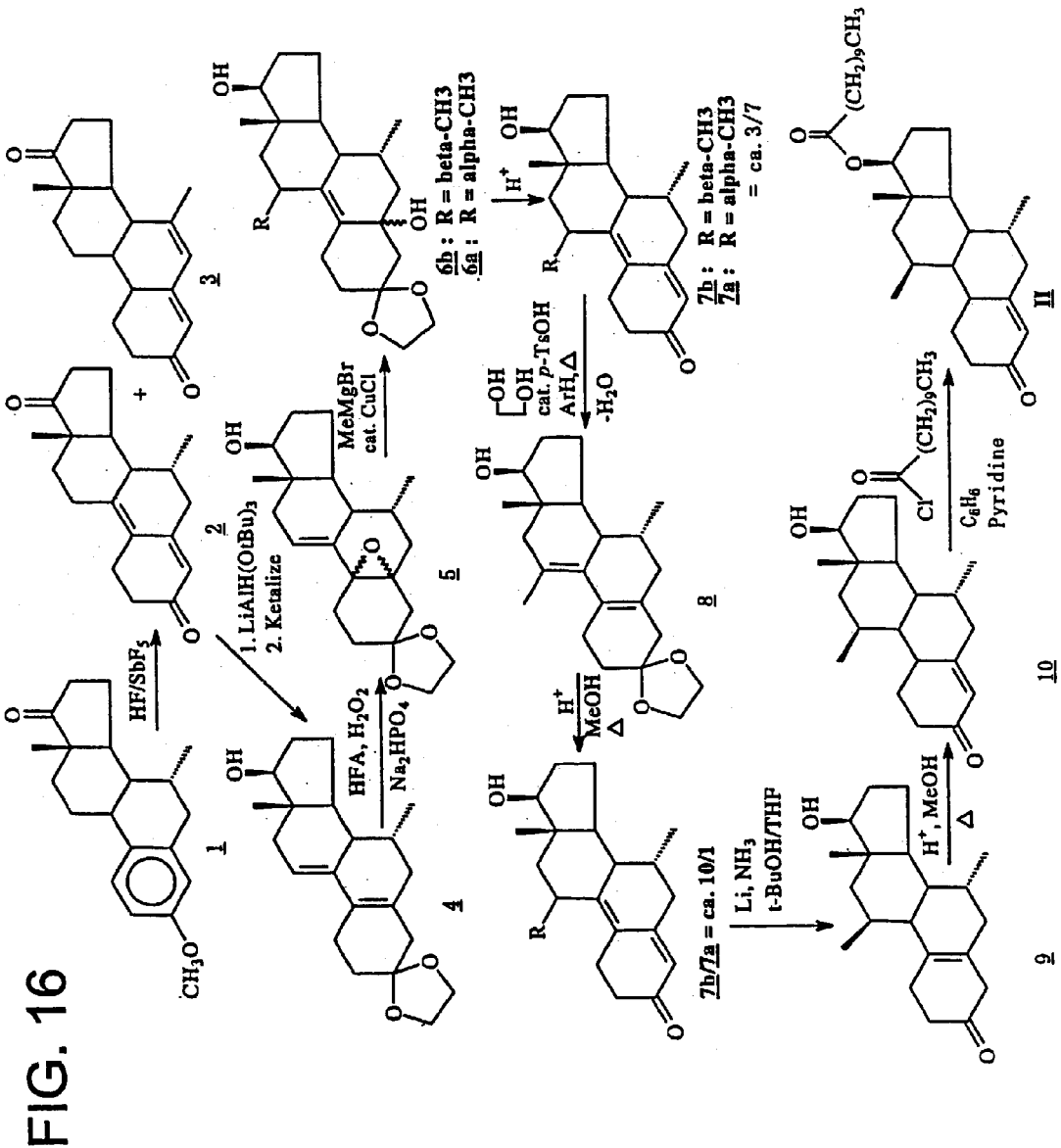
FIG. 16 is a description of a preferred method for preparing 7α,11β-dimethyl-17β-hydroxyestr-4-en-3-one 17-undecanoate.
Figure 17:
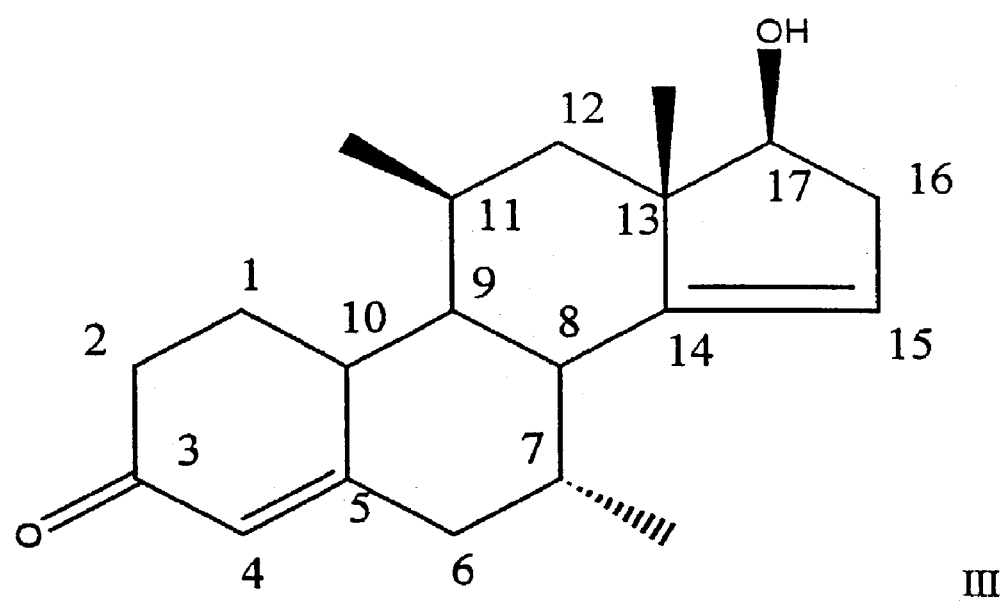
FIG. 17 illustrates the chemical structure of 7α,11β-dimethyl-17β-hydroxyestra-4,14-dien-3-one, with numerals identifying the various carbon atom positions, including the non-alkylated $C_{17}$ position.
Figure 18:
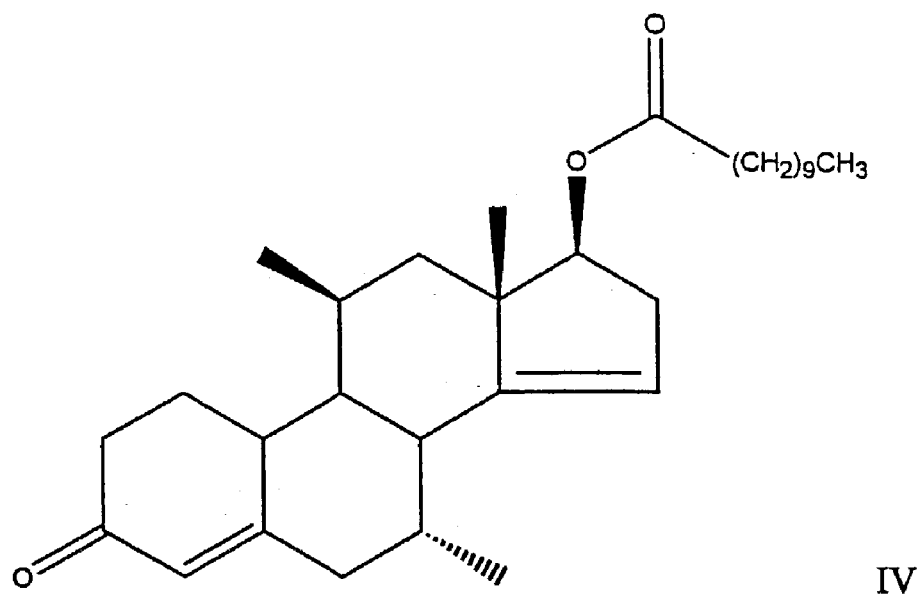
FIG. 18 illustrates the chemical structure of 7α,11β-dimethyl-17β-hydroxyestra-4,14-dien-3-one 17-undecanoate.
Figure 19:
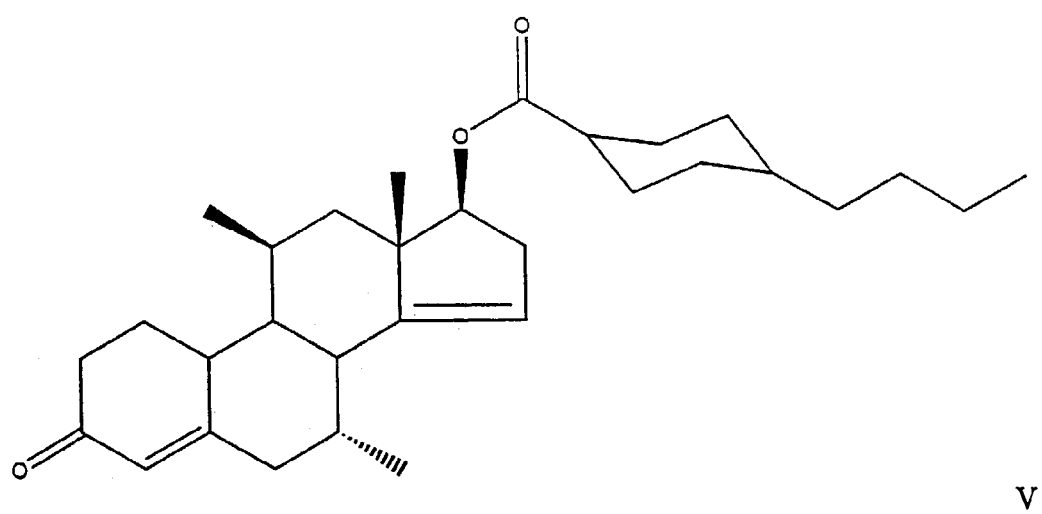
FIG. 19 illustrates the chemical structure of 7α,11β-dimethyl-17β-hydroxyestra-4,14-dien-3-one 17β-4-n-butylcyclohexanecarboxylate.

Turning to FIG. 16, a preferred synthesis route for the preparation of the undecanoate is set forth. This synthesis comprises steps (a)–(g) used in the bucyclate synthesis as set forth above. Thereafter, however, Compound 10 is esterified to provide Compound II (the undecanoate).

The preferred synthesis of 7α,11β-dimethyl-17β-hydroxyestra-4,14-diene-3-one (Compound III) is also provided as a further aspect of the present invention. Generally, this synthesis comprises the steps of:-

A method for preparing 7α,11β-dimethyl-17β-hydroxyestra-4,14-dien-3-one (III) comprising the steps of:

(a) acetylating, aromatizing and hydrolyzing Compound 101

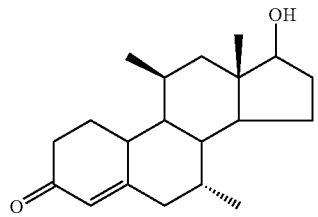
(101)

to provide Compound 102;

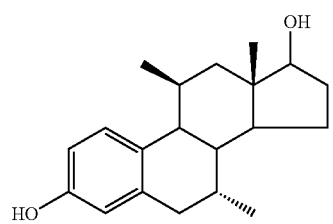
(102)

(b) methylating the phenolic functionality of Compound 102 and oxidizing the hydroxyl group to provide Compound 103;

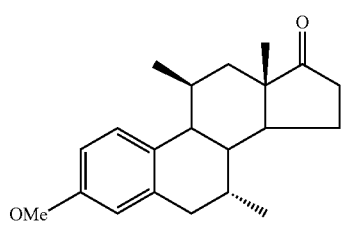
(103)

(c) dehydrogenating Compound 103 to provide Compound 104;

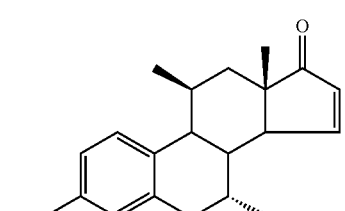
(104)

(d) enolacetylating Compound 104 to provide Compound 105;

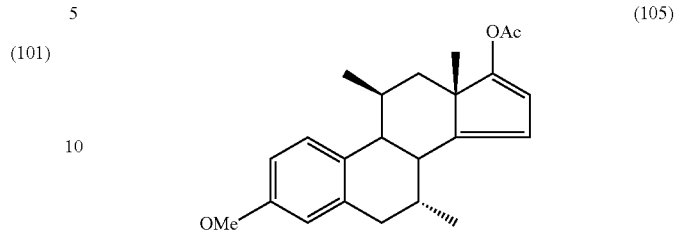
(105)

(e) reducing and hydrolyzing Compound 105 to provide Compound 106; and

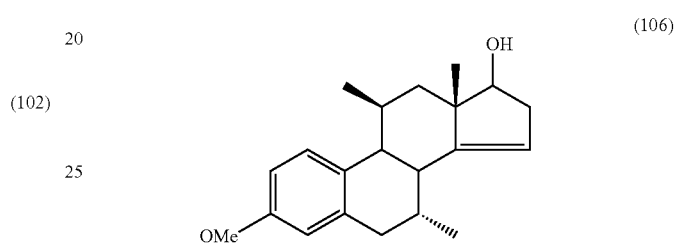
(106)

(f) reducing Compound 106 to provide 7α,11β-dimethyl-17β-hydroxyestra-4,14-dien-3-one (Compound III).

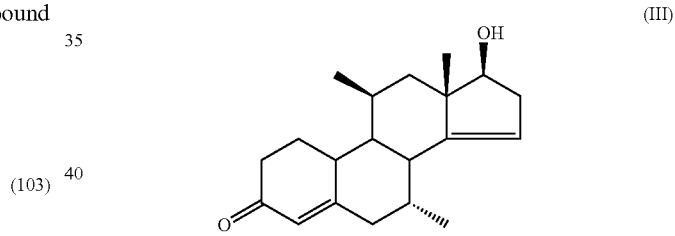
(III)

The foregoing process may further comprise the step of esterifying Compound III by any suitable means to provide 17 esters thereof, preferably 7α,11β-dimethyl-17β-hydroxyestra-4,14-dien-3-one 17-undecanoate (Compound IV) and 7α,11β-dimethyl-17β-hydroxyestra-4,14-dien-3-one 17β-4-n-butylcyclohexanecarboxylate (Compound V).

One or more of the intermediates formed during the foregoing synthesis routes are also contemplated as part of the present invention, and particularly the preferred crystalline forms of those intermediates. In addition, certain of the process steps, and combinations thereof, which provide advantages such as relatively high yields and/or purities of intermediates, constitute further aspects of the present invention. Other aspects of the present invention contemplate crystalline forms of the actives.

A pharmaceutically acceptable carrier is advantageously combined with each active to ease the administration of the active to a patient in need. Suitable carriers for oral and buccal dosage forms, such as tablets, capsules, caplets and soft gelcaps (having an oily carrier), are well known, and may be used in connection with the actives. Preferably, oral dosage formulations of the actives include an oily carrier, and are provided in the form of a soft gelcap, as this formulation was found to enhance the beneficial properties of the actives upon oral administration. Illustrative of oily substances that may be used to provide an oily carrier include, but are not limited to, vegetable oils, e.g. olive oil, safflower oil, corn oil, sunflower oil, cotton seed oil, tsubaki oil, rice bran oil, soybean oil, sesame oil, wheat germ oil, coconut oil, peanut oil, rape seed oil and the like, fish oils, e.g., cuttlefish oil, cod oil, and the like, liver oils, e.g., shark liver oil, cod liver oil and the like, blubber oils, e.g., seal oil, blue whale oil, etc.), conchiferas oils, e.g., abalone oil, oyster oil, and the like, medicinal oily substances, e.g., castor oil, fatty acid glycerides, vitamin E, vitamin A, vitamin K, and the like, polyethylene glycol and the like, and mixtures thereof.

For parenteral administration, any type of carrier that maintains the benefits of the invention as described herein may be used. Preferably, however, and as previously mentioned, the bucyclate, undecanoate, 7α,11β-dimethyl-17β-hydroxyestra-4,14-dien-3-one and/or crystalline 17 esters thereof, is suspended in an aqueous carrier suitable for injection. The water component of the aqueous carrier should constitute at least half thereof, on a weight percent basis, preferably at least about 80 wt.%, and more preferably at least about 90 wt.% of the aqueous carrier. Illustrative of a preferred parenteral formulation is one that includes up to 300 mg of the active suspended in about 1 ml of an aqueous carrier. An illustrative aqueous carrier may be prepared by combining: 1 g benzyl alcohol, 0.5 g sodium carboxyethyl cellulose 50, 0.376 g disodium hydrogen phosphate dihydrate, 1.495 g sodium dihydrogen phosphate dihydrate, with water for injection (WFI) being added to bring volume of the aqueous carrier up to 100 ml.

When formulated as an injectable, the active may be provided in any suitable form, e.g., lyophilizate, dry powder for reconstitution, a ready-to-use liquid, and in any suitable container, e.g., vial, pre-filled syringe, or the like.

The actives may also be administered transdermally. Transdermal delivery devices are well known. Illustrative transdermal devices are described in U.S. Pat. Nos. 5,635, 203 and 6,024,976. When a transdermal delivery device is used, the amount of the active included in the device for therapy should range from about 5% to about 25% of the parenteral dose, and preferably from about 10% to about 20% of that dose, as set forth herein.

The following examples are provided as further illustration of the present invention, but should not be construed as limiting the invention in any respect.

EXAMPLE 1

This example provides data on the androgenic potency of 7α,11β-dimethyl-17β-hydroxy-4-estren-3-one bucyclate (CDB-4386A), its free alcohol (CDB-1321 D), testosterone bucyclate (CDB-1781 V-1), methyltestosterone (CDB-110), testosterone (CDB-111 C) and testosterone enanthate (CDB-112a) when administered orally.

Immature (about 21-day-old) Sprague-Dawley rats were orchidectomized under anesthesia, and randomly assignee to groups of ten animals for each dose level of the active undergoing testing. Each active was dissolved in 10% ethanol/sesame oil and administered by gavage (oral) each day for seven days beginning on the date of the orchidectomy. The animals were sacrificed 24 hours after the last dose, and the ventral prostate and seminal vesicles were excised, cleaned of fat and connective tissue, blotted on moist filter paper and weighed to the nearest 0.1 mg. See, e.g., Hershberger, L. et al, Myotrophic Activity of 19-nortestosterone And Other Steroids Determined By Modified Levator And Muscle Method, *Proc. Soc. Exptl. Biol. Med* 83 175–180 (1953). Regression analysis was performed by conventional methods using a PROPHET data management system. See, e.g., Bliss, C., The Statistics of Bioassay (Academic Press, New York, 1952); Hollister, C., *Nucleic Acids Res.* 16 1873–75 (1988). Ventral prostate weight was used as the endpoint because it is the sensitive organ to androgenic stimulation.

Figure 3:
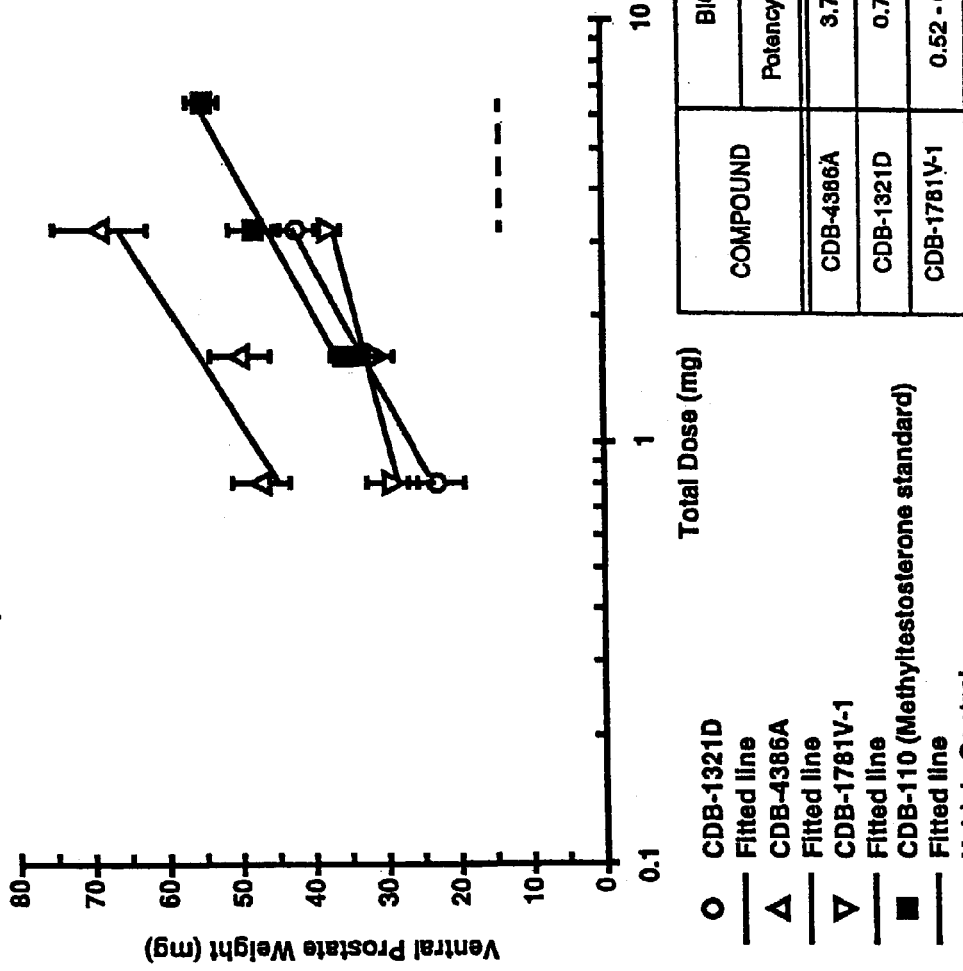
FIG. 3 is a graph comparing the androgenic potency of 7α,11β-dimethyl-17β-hydroxy-4-estren-3-one bucyclate and that of other compounds after oral administration.
Figure 4:
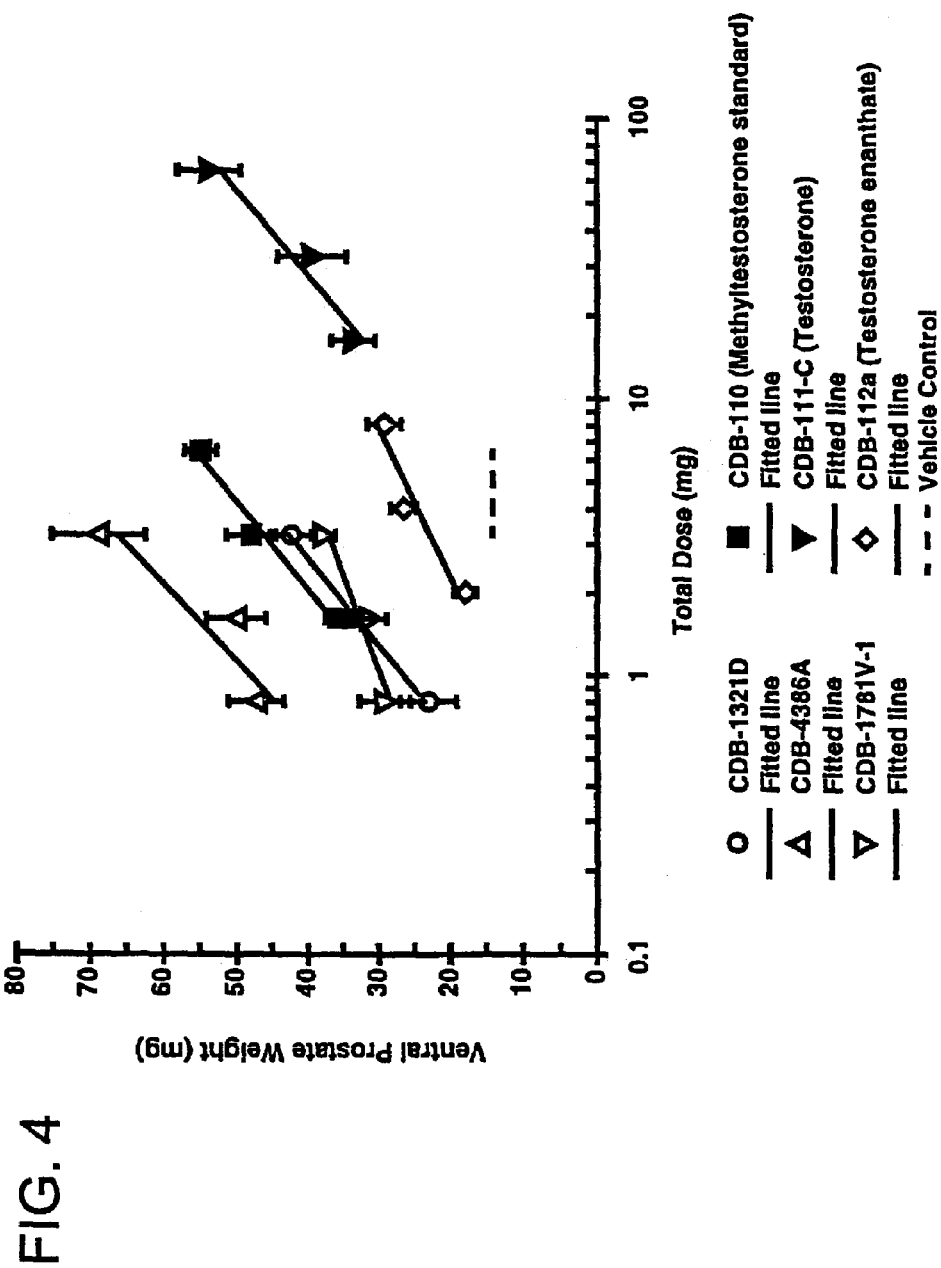
FIG. 4 is a graph comparing the androgenic potency of 7α,11β-dimethyl-17β-hydroxy-4-estren-3-one bucyclate and that of other compounds after oral administration.

The data obtained from this study is presented in graphic form in FIGS. 3 and 4. This data indicates that the oral androgenic activity of 7α,11β-dimethyl-17β-hydroxy-4-estren-3-one bucyclate is about 4 times (3.77 times, at a 95% confidence interval 2.25–6.33) as potent as methyltestosterone and at least 4 times as potent as the free alcohol (1321 D), and testosterone bucyclate (1781 V-1). 7α,11β-dimethyl-17β-hydroxy-4-estren-3-one bucyclate is also about 10–100 times more potent than testosterone itself (111-C) or testosterone enanthate (112a) administered orally.

EXAMPLE 2

This example provides data that demonstrates the duration of activity of 7α,11β-dimethyl-17β-hydroxy-4-estren-3-one bucyclate (CDB-4386A) compared to its free alcohol (CDB-1321 D), the 11α-methyl analog of 7α,11β-dimethyl-17β-hydroxy-4-estren-3-one bucyclate (CDB-4386), testosterone bucyclate (CDB-1781a, -1781 V2), and testosterone enanthate (CDB-112E) when administered parenterally (by subcutaneous injection).

Immature (about 21-day-old) Sprague-Dawley rats were orchidectomized under anesthesia, and randomly assignee to groups of ten animals for each dose level of the active undergoing testing. Each active was administered by subcutaneous injection each day for seven days beginning on the date of the orchidectomy. The animals were sacrificed 24 hours after the last dose, and the ventral prostate and seminal vesicles were excised, cleaned of fat and connective tissue, blotted on moist filter paper and weighed to the nearest 0.1 mg. Regression analysis was performed by conventional methods using a PROPHET data management system. Ventral prostate weight was used as the endpoint because it is the sensitive organ to androgenic stimulation.

Except for testosterone enanthate, each active was formulated in two different carriers: (1) an aqueous suspension and (2) in sesame oil. Testosterone enanthate was formulated using the sesame oil carrier only, because it exists as a liquid at room temperature and could not therefore be formulated as an aqueous suspension.

The carrier used to provide the aqueous suspension was formulated as follows: 1 g benzyl alcohol, 0.5 g sodium carboxyethyl cellulose 50, 0.376 g disodium hydrogen phosphate dihydrate, 1.495 g sodium dihydrogen phosphate dihydrate, with water for injection (WFI) being added to bring volume of the carrier up to 100 ml.

Each formulation was prepared at a concentration of 0.6 mg/0.2 ml. To obtain further comparative data, testosterone bucyclate was formulated in the aqueous suspension at a higher dose (1.0 mg/0.2 ml).

Figure 5:
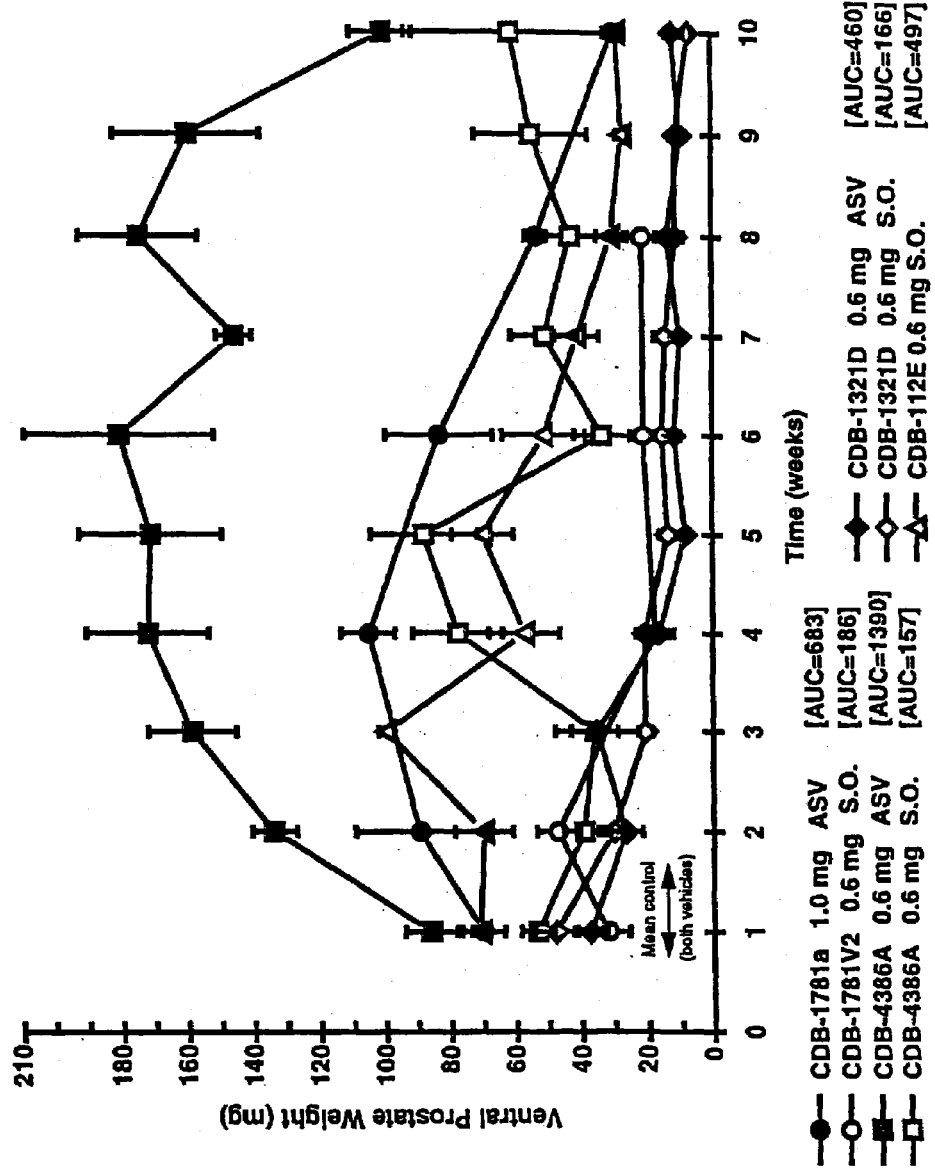
FIG. 5 is a graph comparing the duration of activity of 7α,11β-dimethyl-17β-hydroxy-4-estren-3-one bucyclate and that of other compounds after subcutaneous injection.

The results, shown graphically in FIG. 5, substantiate the unexpected activity of 7α,11β-dimethyl-17β-hydroxy-4-estren-3-one bucyclate (CDB-4386A) as compared to other androgenic esters. The former exhibits activity in both potency and duration that far exceeds the activity exhibited by the comparative esters when administered in the same amounts, and particularly when 7α,11β-dimethyl-17β-hydroxy-4-estren-3-one bucyclate is formulated as an aqueous suspension. The activity of even CDB-4386, which may be referred to as "close" to 7α,11β-dimethyl-17β-hydroxy-4-estren-3-one bucyclate from a chemical structure perspective, nevertheless exhibits relatively low activity as compared to 7α,11β-dimethyl-17β-hydroxy-4-estren-3-one bucyclate.

Further, both the potency and long-term activity of the higher dosage of testosterone bucyclate (1.0 mg) was significantly less than that provided by the lower dosage of 7α,11β-dimethyl-17β-hydroxy-4-estren-3-one bucyclate (0.6 mg) in an aqueous suspension.

EXAMPLE 3

This example illustrates the relative androgenic activity of testosterone and its derivatives.

Immature (about 21-day-old) Sprague-Dawley rats were orchidectomized under anesthesia, and randomly assignee to groups of ten animals for each dose level of the active undergoing testing. Each active was dissolved in 10% ethanol/sesame oil and administered by gavage (oral) or subcutaneous injection each day for seven days beginning on the date of the orchidectomy. The animals were sacrificed 24 hours after the last dose, and the ventral prostate and seminal vesicles were excised, cleaned of fat and connective tissue, blotted on moist filter paper and weighed to the nearest 0.1 mg. Regression analysis was performed by conventional methods using a PROPHET data management system. Ventral prostate weight was used as the endpoint because it is the sensitive organ to androgenic stimulation.

Figure 6:
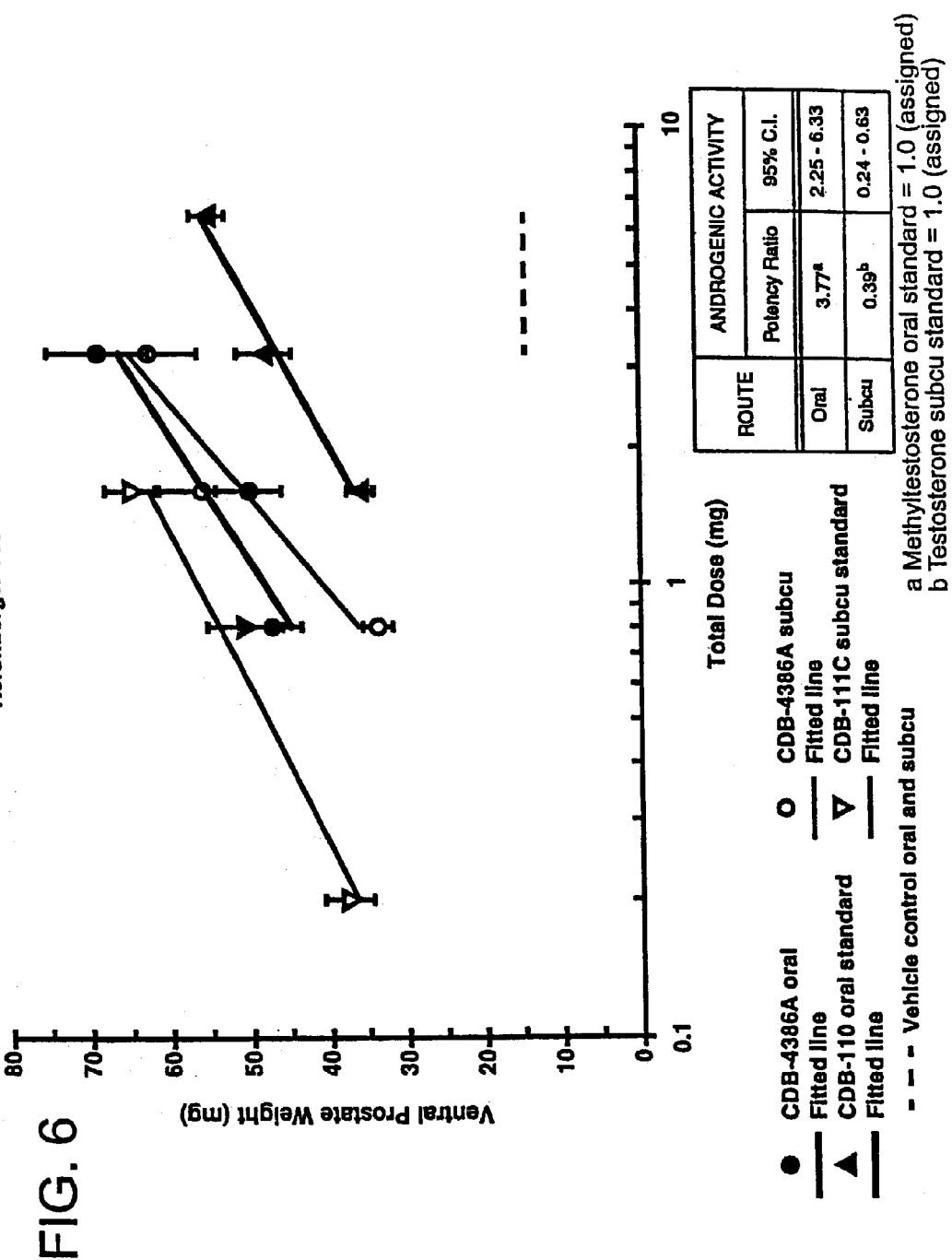
FIG. 6 is a graph comparing the androgenic potency of 7α,11β-dimethyl-17β-hydroxy-4-estren-3-one bucyclate and that of other compounds after oral and subcutaneous injection.
Figure 7:
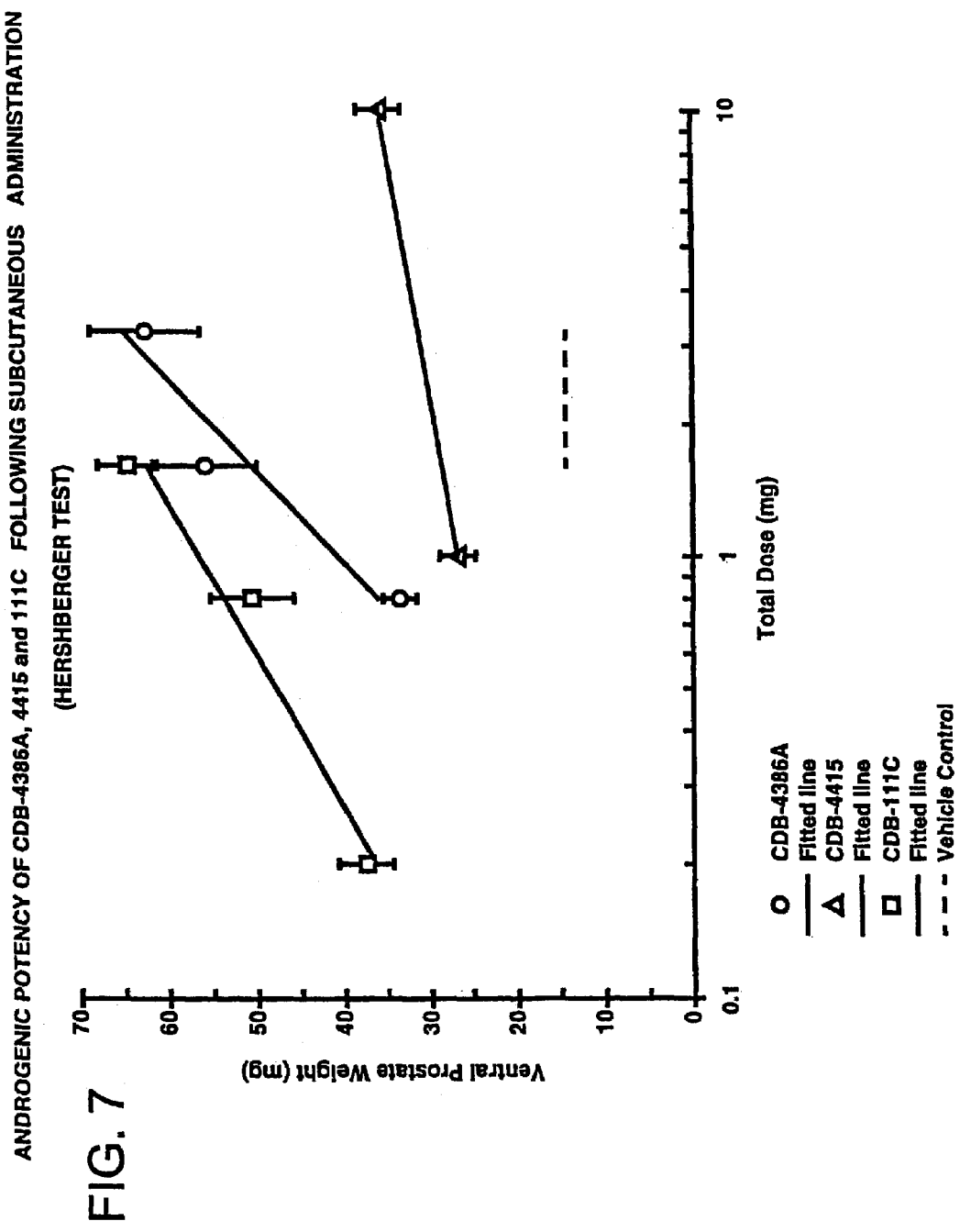
FIG. 7 is a graph comparing the androgenic potency of 7α,11β-dimethyl-17β-hydroxy-4-estren-3-one bucyclate and that of other compounds after subcutaneous injection.

FIGS. 6 and 7 are graphic representations of the androgenic assays of the actives. Each data point represents the mean (n=10) and standard error of the mean (SEM) for each prostate weight for each dose level.

From the data, 7α,11β-dimethyl-17β-hydroxy-4-estren-3-one bucyclate (CDB-4386A) exhibited almost four times the oral activity of methyltestosterone (CDB-110) (3.77 times, at 95% C.I. 2.3–6.3), the current oral standard. However, 7α,11β-dimethyl-17β-hydroxy-4-estren-3-one bucyclate demonstrated only 0.4 times the activity of testosterone (CDB-111C) following subcutaneous administration (0.4 times, at 95% C.I. 0.2–0.6). The oral findings were unexpected because testosterone and its esters exhibit low activity upon oral administration.

The relatively weak activity upon subcutaneous administration was also unexpected in view of the results on the long-acting activity of 7α,11β-dimethyl-17β-hydroxy-4-estren-3-one bucyclate in Example 5. Testosterone, on the other hand, exhibited the expected level of activity after subcutaneous injection. The weak activity of the 11α-methyl analog of 7α,11β-dimethyl-17β-hydroxy-4-estren-3-one bucyclate (CDB-4386) after subcutaneous administration indicates the importance of the stereoconfiguration of the 7α,11β-dimethyl-17β-hydroxy-4-estren-3-one bucyclate (CDB-4386A) molecule.

Although not desiring to be bound to any particular theory, the oral activity of 7α,11β-dimethyl-17β-hydroxy-4-estren-3 -one bucyclate may be due to its resistance to degradation in the gastrointestinal tract and/or rapid metabolism by the liver. It is also possible that the lipophilic nature of 7α,11β-dimethyl-17β-hydroxy-4-estren-3-one bucyclate permits absorption of the active into the thoracic lymph, thereby avoiding direct entrance into the portal system and metabolism by the liver.

Further, the lack of activity experienced by 7α,11β-dimethyl-17β-hydroxy-4-estren-3-one bucyclate under subcutaneous administration may reflect the slow release, and possibly metabolism, of the active from the injection site over the relatively brief 7-day administration period. This same property, however, conveys long-acting activity on 7α,11β-dimethyl-17β-hydroxy-4-estren-3-one bucyclate after parenteral administration in an aqueous vehicle.

In addition to the foregoing, the androgenic potency and relative binding affinity to the androgen receptor of several free alcohols after subcutaneous administration of their corresponding esters was also determined. The results are presented in the following Table.

| Ester Compound | | Activity of Corresponding Alcohol | |
|---|---|---|---|
| Compound ID | Melting Point (° C.) | Relative Binding Affinity[1] | Androgenic Potency[2] |
| A | 68–69 | 91 | 8.1[3] |
| B | 129–130 | no data | 1.2 |
| C | oil | 148 | 61.1 |
| D | 108 | no data | 36.4–61.7[3] |
| E | 99–100 | 1 | no data |
| F | 130–132 | 82 | 19.3 |
| G | 134–136 | 28 | 1.0 (assigned) |

[1]From rat prostate; relative to methyltrienolone = 100% (androgenic potency = 5.0)
[2]Ventral prostate weight assay following subcutaneous administration.
[3]Did not pass one or more significance tests (p < 0.05)
[4]Reference compound
A: 7α-Methyl-19-nortestosterone-17β-bucyclate
B: 7α-Methyl-5α-dihydro-19-nortestosterone-17β-bucyclate
C: 7α-Methyl-14-dehydro-testosterone-17β-bucyclate
D: 7α-Methyl-D-homo-testosterone-17β-bucyclate
E: 7α, 11α-Dimethyl-19-nortestosterone-17β-bucyclate
F: 7α, 11β-dimethyl-17β-hydroxy-4-estren-3-one bucyclate (CDB-4386A)
G: Testosterone bucyclate The foregoing data demonstrates that the activity of a particular androgenic bucyclate ester (such as 7α,11β-dimethyl-17β-hydroxy-4-estren-3-one bucyclate, CDB-4386A) cannot be predicted on the basis of the androgenic activity of its corresponding free alcohol. More specifically, the superior activity of 7α,11β-dimethyl-17β-hydroxy-4-estren-3-one bucyclate could not have been predicted from this data.

EXAMPLE 4

This example further illustrates the relative activity of various testosterone esters, including 7α,11β-dimethyl-17β-hydroxy-4-estren-3-one bucyclate, over relatively long periods of time.

Immature (about 21-day-old) Sprague-Dawley rats were orchidectomized under anesthesia, and randomly assignee to groups of 40 or more. Animals received a single subcutaneous injection of 0.6 mg of each ester in 0.2 ml of an aqueous suspending carrier and/or oily carrier (10% ethanol/90% sesame oil or ethyl oleate) on the date of the orchidectomy. In cases where the ester was not solid at room temperature, 10% ethanol/sesame oil or ethyl oleate was used as the carrier. In this example, the carrier used to provide the aqueous suspension was formulated as follows: 1 g benzyl alcohol, 0.5 g sodium carboxylethyl cellulose 50, 0.376 g disodium hydrogen phosphate dihydrate, 1.495 g sodium dihydrogen phosphate dihydrate, with water for injection (WFI) being added to bring volume of the carrier up to 100 ml.

Five animals from each group were sacrificed at weekly or biweekly intervals, and the ventral prostate and seminal vesicles were excised, cleaned of fat and connective tissue, blotted on moist filter paper and weighed to the nearest 0.1 mg.

Ventral prostate weight was used as the endpoint because it is the sensitive organ to androgenic stimulation. Regression analysis was performed by conventional methods using the PROPHET data management system previously identified.

Figure 8:
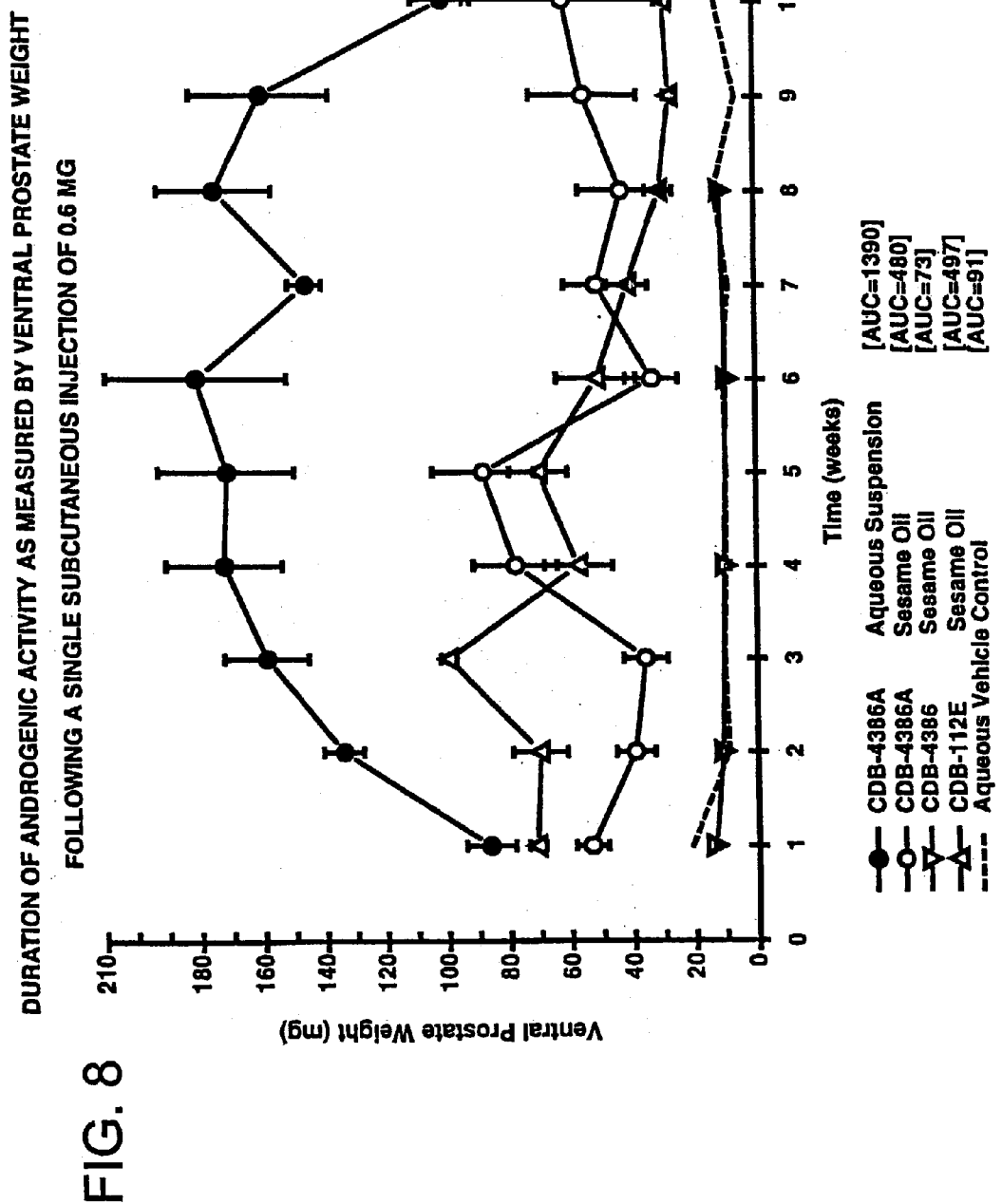
FIG. 8 is a graph comparing the duration of activity of 7α,11β-dimethyl-17β-hydroxy-4-estren-3-one bucyclate and that of other compounds after subcutaneous injection.
Figure 9:
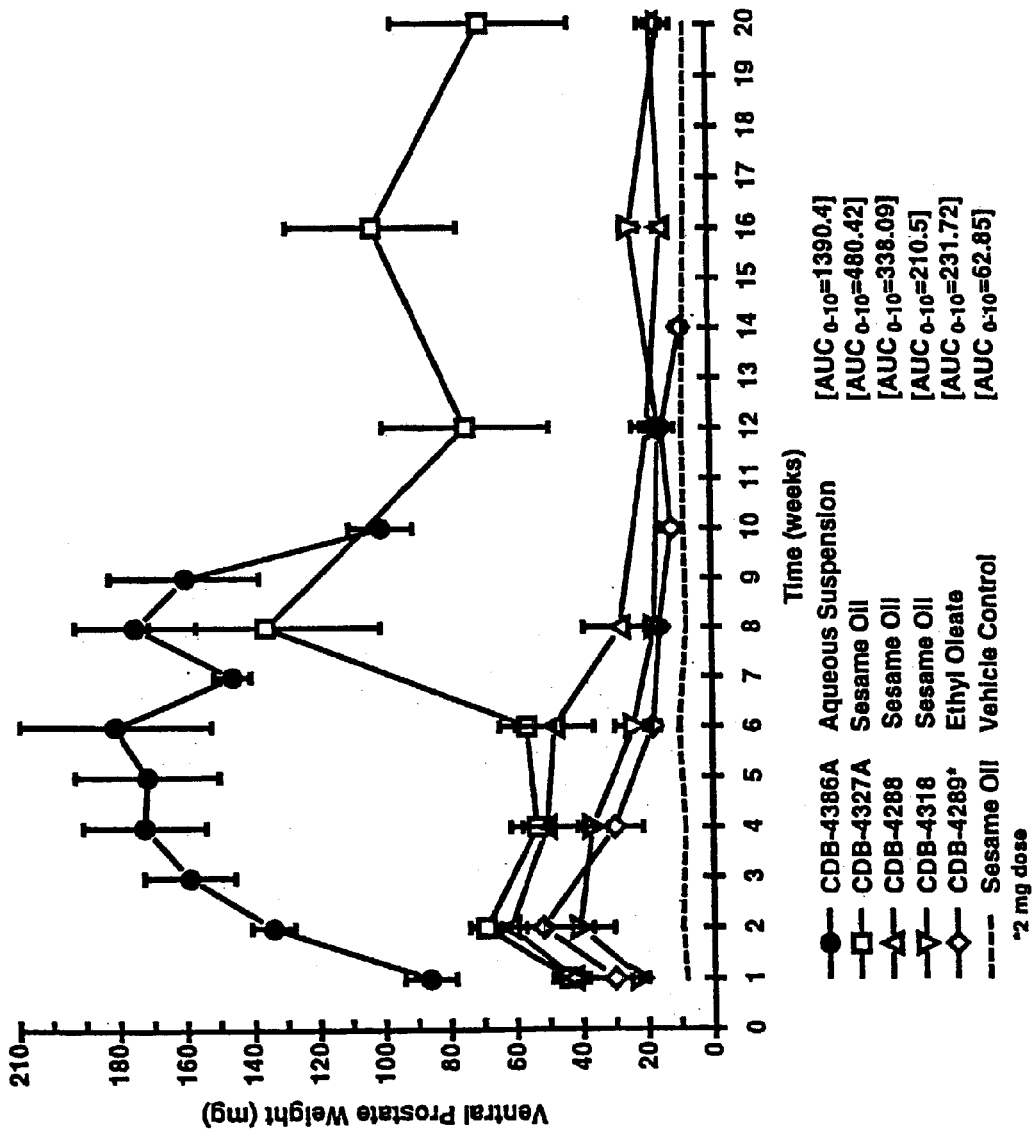
FIG. 9 is a graph comparing the duration of activity of 7α,11β-dimethyl-17β-hydroxy-4-estren-3-one bucyclate and that of other compounds after subcutaneous injection.

FIGS. 8 and 9 are graphic representations of the androgenic assays of the actives. Each data point represents the mean (n=10) and standard error of the mean (SEM) for each prostate weight for each dose level.

FIG. 8 is a graph of the ventral prostate weights at weekly intervals over a 10 week period after the subcutaneous administration of 7α,11β-dimethyl-17β-hydroxy-4-estren-3-one bucyclate (CDB-4386A) in both oily and aqueous carriers, its 11α-methyl analog (CDB-4386) in both carriers, and testosterone enanthate (CDB-112E) in an oily carrier. 7α,11β-dimethyl-17β-hydroxy-4-estren-3-one bucyclate in the aqueous vehicle exhibited the most dramatic increase and maintenance of ventral prostate weight. The area under the curve (AUC, calculated by the trapezoidal rule), was about 3 times greater for 7α,11β-dimethyl-17β-hydroxy-4-estren-3-one bucyclate than for testosterone enanthate in sesame oil. The 11α-methyl analog was inactive in this experiment, with evaluation being discontinued 8 weeks after administration. This experiment highlights the significance of the ability to provide 7α,11β-dimethyl-17β-hydroxy-4-estren-3-one bucyclate in the form of an aqueous suspension, which provides unexpected and desirable long-term androgenic activity. This experiment also underscores the importance of the stereoconfiguration of the $C_{11}$ substituent.

FIG. 9 is a graph of the ventral prostate weights at various time intervals up to 20 weeks after administration of several different bucyclate esters: 7α,11β-dimethyl-17β-hydroxy-4-estren-3-one bucyclate (CDB-4386A), 7α-Methyl-14-dehydro-19-nortestosterone-17β-bucyclate (CDB-4327A), 17α-Methyl-19-nortestosterone-17β-bucyclate (CDB-4288), 7β-Methyl-16-dehydro-D-homo-19-nortestosterone-17β-bucyclate (CDB-4318) and 17α-Methyl-5α-dihydro-19-nortestosterone-17β-bucyclate (CDB-4289). All esters other than 7α,11β-dimethyl-17β-hydroxy-4-estren-3-one bucyclate were administered in the oily carrier because they do not exist as solids at room temperature, or possess low melting points. 7α,11β-dimethyl-17β-hydroxy-4-estren-3-one bucyclate, suspended in the aqueous carrier, exhibited the greatest AUC over the 10-week period for which this parameter was calculated. CDB-4327A demonstrated surprising stimulation of ventral prostate size over the entire 20-week observation period, however, this is one of the most active synthetic androgens presently known. The remaining actives showed relatively weak activity. This experiment can be said to demonstrate that the prediction of activity cannot be based on the structure of the active, or on the carrier used in connection with the administration of the active.

Figure 10:
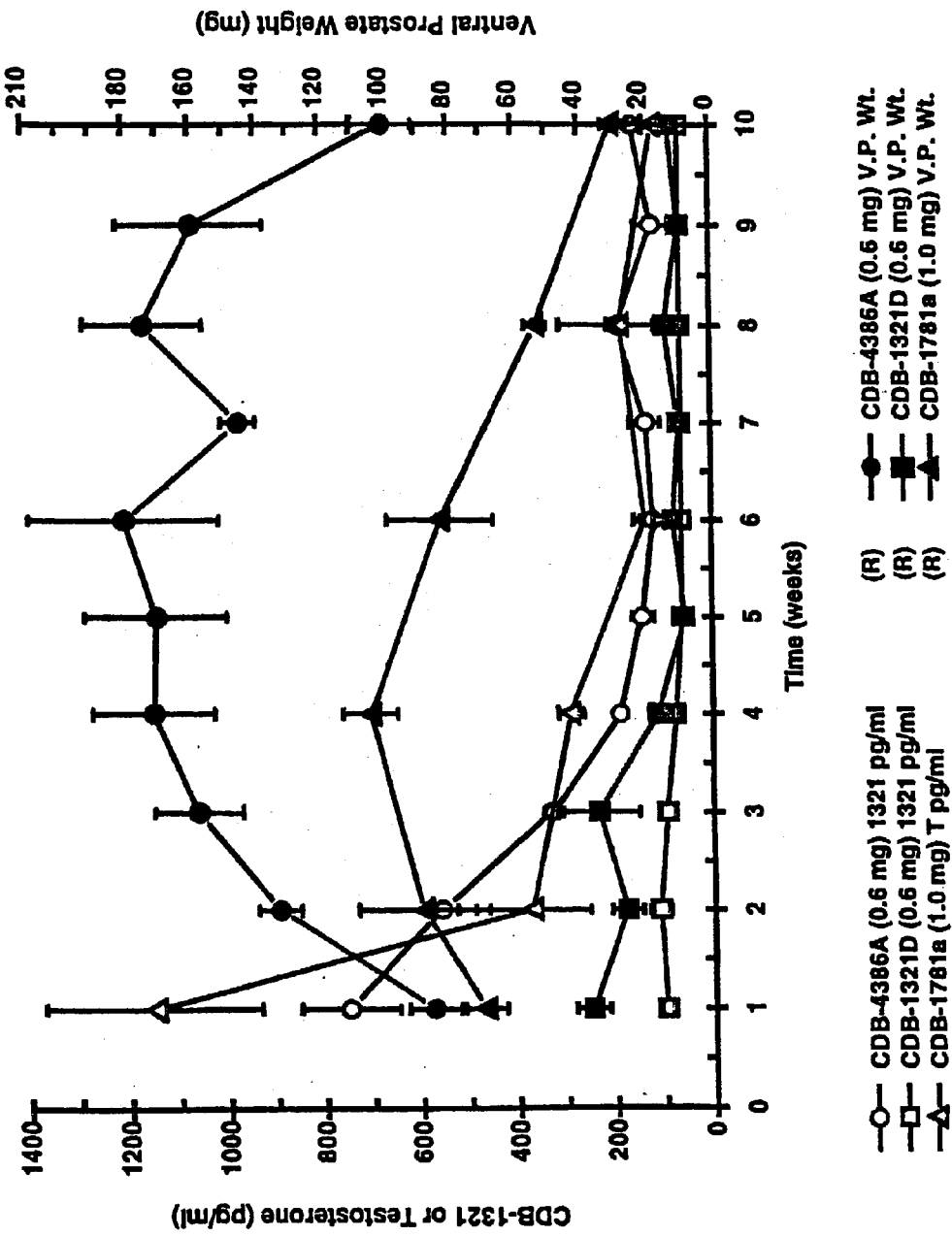
FIG. 10 is a graph comparing testosterone serum levels (pg/ml) after subcutaneous injection of 7α,11β-dimethyl-17β-hydroxy-4-estren-3-one bucyclate and other compounds.

Serum samples taken from the animals at autopsy showed the presence of the free alcohol (7α,11β-dimethyl-19-nortestosterone) which decreased with time over the 10 week observation period. The results are provided in FIG. 10. 7α,11β-dimethyl-17β-hydroxy-4-estren-3-one bucyclate, suspended in the aqueous carrier, provided the highest levels of the free alcohol, and maintained these relatively high levels over the 10-week observation period.

EXAMPLE 6

This example describes a preferred process for synthesizing 7α,11β-dimethyl-17β-hydroxy-4-estren-3-one bucyclate (Compound I). Reference may be made to FIG. 11.

A. Preparation of 7α-Methylestra-4,9-diene-3,17-dione (Compound 2)

Under a nitrogen flush through an inverted plastic funnel the antimony pentafluoride (110 mL, 5.79 mol) was weighed into a Teflon jar. Hydrogen fluoride (436 nL, 21.8 mol), chilled to 4° C., was first collected in a Teflon separatory funnel, then added with extreme care to the reaction vessel under a nitrogen flush. Failure to assure rapid mixing can result in an eruption. As the mixture was stirred, it was cooled to 0° C. for 20 min. 7α-methylestrone methyl ether (Compound 1, 25.0 g, 83.8 mmol) was carefully added under nitrogen. The reaction was stirred at 0° C. for 2.5 hr, after which it was slowly poured into a plastic beaker containing a mixture of saturated potassium carbonate (300 mL, 900 g/1000 mL) and ice. Additional potassium carbonate was used to adjust the pH to ca. 8. This mixture was then extracted with methylene chloride (3×) and the organic portions were washed with water and brine. After drying over sodium sulfate, the solvent was removed in vacuo to give 24.8 g of crude oil. This crude material contains Compound 2 and an isomeric by-product, 4,6-diene-dione-3,20 (Compound 3) in a 2:1 ratio. Therefore, the crude material was subjected to dry column chromatography on silica gel (63–200 mesh) eluted with 3% acetone in $CH_2Cl_2$. This gave a segment which contained 15 g of the desired product (Compound 2). After extraction, evaporation of the solvent followed by trituration with ether afforded 9.24 g of Compound 2 in 38.8% yield. The mother liquor from this material was combined with the other principle portion of the column, and was rechromatographed using the same conditions. Trituration of the segments provided an additional 0.19 g of the desired product (Compound 2). Total amount was 9.43 g in 39.6% yield; m.p. 204–2050° C. (Lit. m.p.=(8). FRIR (KBr, diffuse reflectance): $V_{max}$ 3454, 3282, 3030, 2968, 2928, 2902, 1737, 1652, 1600, and 1580 $cm^{-1}$. NUR ($^1H$, $CDCl_3$) δ 0.859 (d, 3 H, J=3.5 Hz), C7α-$CH_3$), 1.001 (s, 3 H, C18-$CH_3$) and 5.726 (s, 1 H, C4-CH). NMR ($^{13}C$, $CDCl_3$) δ 12.641, 21.835, 24.885, 25.576, 28.021, 30.626, 35,621, 36.893, 39.416, 42.4779, 45.966, 123.259 (C-4), 126.081 (C-10)m 140.295 (C-9), 154.572 (C-5), 199.052 (C-3) and 219.633 (C-17).

B. The Preparation of 3,3-Ethylenedioxy-7α-methyl-17β-hydroxyestra-5(10),9(11)-diene (Compound 4)

A THF (500 mL) solution of the dione (Compound 2, 10.0 g, 35.16 mmol) was chilled to 0° C. and treated dropwise with a THF solution of lithium tri-tert-butoxyaluminum hydride (1.0 M/THF, 40.0 mL. 8.9 mmol). The mixture was stirred at 0° C. for 2 hr. EtOAc (10.0 mL) was added and most of the solvent was removed in vacuo. The residue was diluted with cold 0.1 N HCl and the aqueous mixture was extracted with EtOAc (3×). The EtOAc layers were washed with water and brine, combined, and dried over sodium sulfate. Evaporation of the solvent gave 10.61 g of a stable foam. The material was then dissolved in benzene (1 L). Ethylene glycol (10.0 mL) was added, followed by p-toluenesulfonic acid (500 mg). The resulting mixture was heated to reflux while draining off approximately 500 mL of benzene from the Dean-Stark trap. The mixture was cooled and diluted with saturated sodium bicarbonate solution. The benzene solution was washed with water and brine. The aqueous washes were extracted with EtOAc (2×). The combined organic extracts were dried over sodium sulfate. Evaporation of the solvent gave the 12.61 g of a stable foam. The material was chromatographed (5% acetone in $CH_2Cl_2$) to afford 10.05 g of the ketal (Compound 4) in 87% yield. NMR ($CDCl_3$) δ 0.725 (s,3 H, C18-CH3), 0.727 (d,3 H, J=7.2 Hz, C7α-$CH_3$), 3.777(t ,1 H, J=8.7 Hz, C17α-CH), 3.979 (m, 4 H, 3-Ketal) and 5.638 (m, 1 H, Cll=CH). MS (EI) m/z: relative intensity: 330 ($M^{30}$).

C. Preparation of 3,3-ethylenedioxy-7α-methyl-5α,10α-epoxy-17β-hydroxyestra-9(11)-ene (Compound 5)

A solution of hexafluoroacetone (30.0 g, 136.2 mmol) in $CH_2Cl_2$, (150 mL) was chilled to 0° C. With vigorous stirring, 30% hydrogen peroxide (14.0 mL, 136.2 mmol) and solid disodium hydrogen phosphate (5.86 g, 41.30 mmol) was added. The resulting mixture was stirred at 0° C. for ½ hr. A solution of the ketal (Compound 4, 15.0 g 45.39 mmol) in $CH_2Cl_2$ (300 mL) was added and the mixture was stirred at 4° C. for 24 hr. The mixture was then diluted with 10% sodium sulfite solution, and subsequently extracted with $CH_2Cl_2$ (3×). The extracts were washed with water and brine, combined and dried over sodium sulfate. Evaporation of the solvent gave 16.26 g. of Compound 5. This material was used without further purification in the subsequent reaction. NMR ($CDCl_3$) δ 0.725 (s, 3 H, C18-$CH_3$), 0.762 (d, 3 H, J=7.2 Hz, C7α-$CH_3$), 3.758 (t, 1 H, J=8.7 Hz, C17α-CH), 3.895 (d, 4 H, 3-ketal) and 6.00 (m, 1 H, C11=CH).

D. Preparation of 3,3-ethylenedioxy-7α,11β-dimethyl-5α,17β-dihyrdoxyestra-9-ene (Compound 6)

A solution of methylmagnesiumbromide (1.4 M THF/toluene, 210 mL, 295 mmol) was added to THF (150 mL) and copper (I) chloride (2.92 g, 29.5 mmol) was added. After stirring at room temperature for ½ hr, a solution of the epoxide (Compound 5, 16.26 g 46.99 mmol) in THF (450 mL) was added dropwise over 5 min. The mixture was stirred at room temperature for 3 hr. The mixture was diluted with saturated ammonium chloride solution and air was bubbled through the mixture for ½ hr to oxidize Cu(I) to Cu(II). The aqueous mixture was extracted with ether (3×). The ether extracts were washed with water and brine, combined, and dried over sodium sulfate. Evaporation of the solvent gave 16.70 g of a yellow semi-solid. The material was triturated with ether and the solid was filtered to afford 8.86 g of a mixture of Grignard products (7α,11α-dimethyl and 7α,11β-dimethyl, referred to as Compounds 6a and 6b, respectively). Evaporation of the filtrate gave 7.4 g of a stable foam. Total amount was 16.26 g in quantitative yield.

E. Hydrolysis of a Mixture of Compounds 6a and 6b to Isomeric Compounds 7b and 7a (as a ca. 3/7 mixture)

The solid (containing Compounds 6a and 6b) from Step D above 16.26 g, 54.2 mmol) was dissolved in acetic acid/THF/water (3:1:1, 500 mL) and heated to reflux for 2 hr. The solvent was evaporated in vacuo and the mixture was diluted with saturated sodium bicarbonate solution. The mixture was then extracted with $CH_2Cl_2$. The $CH_2Cl_2$ extracts were washed with water, brine, combined, and dried over sodium sulfate. Evaporation of the solvent gave 7.45 g. The material was chromatographed 10% acetone/methylene chloride) to afford 5.12 g of Compounds 7a and 7b (7α,11α-dimethyl and 7α,11β-dimethyl, respectively). The foam obtained in Step D was treated in the same manner to afford an additional 2.73 g of Compounds 7a and 7b after chromatography. Total amount was 7.85 g in 45.9% yield. NMR ($CDCl_3$) δ 0.747 (d, 3 H, J=7 Hz, C7α-$CH_3$), 0.780 (s, 3 H, C18-$CH_3$of Compound 6b), 0.963 (s, 3 H, C18-$CH_3$ of Compound 6a), 1.077 (d, 3 H, J=7 Hz, C11α-$CH_3$), 1.173 (d, 3 H, J=7 Hz, C11β-$CH_3$), and 3.770 (t, 1 H, J=8.7 Hz, C17α-CH.

F. Preparation of 3,3-Ethyleniedioxy-7α,11-dimethyl-17β-hydroxyestra-5(10),9(11)-diene (Compound 8)

A solution of Compounds 7a/7b (2.0 g 6.65 mmol) in benzene (500 mL) was treated with ethylene glycol (5.0 mL) and p-toluenesulfonic acid (250 mg). The mixture was heated at reflux with azeotropic removal of water. Approximately 250 mL of solvent was distilled off. The mixture was cooled to room temperature and diluted with saturated sodium bicarbonate solution. The mixture was extracted with EtOAc. The EtOAc extracts were washed with water and brine, combined and dried over sodium sulfate. Evaporation of the solvent gave 2.15 g of stable foam in 93.9 % yield. The material was homogeneous by TLC and less polar than the starting material. NNM ($CDCl_3$) δ 0.716 (s, 3 H, C18-$CH_3$), 0.725 (d, 3 H, J=7.2 Hz, C7α-$CH_3$), 1.801 (br s, 3 H, C11-$CH_3$), 3.755 (t, 1 H, J=8.7, C17α-CH) and 4.003 (m, 4 H, 3-ketal).

G. Preparation of 7α,11β-Dimethyl-17β-hydroxyestra-4,9-diene-3-one (Compounds 7b/7a, ca. 10/1) via Hydrolysis of Compound 8

The ketal (Compound 8, 2.15 g 6.24 mmol) was dissolved in methanol 200 mL) and 10.0 mL of 10% HCl was added. The solution was heated at reflux for 18 hr. The solvent was evaporated in vacuo and the residue was diluted with saturated sodium bicarbonate solution. The aqueous mixture was extracted with $CH_2Cl_2$. The methylene chloride extracts were washed with water and brine, combined and dried over sodium sulfate. Evaporation of the solvent gave 1.89 g of a stable foam. The material was chromatographed (10% acetone in $CH_2Cl_2$) to afford 950 mg, of the 7α,11β-dimethyl compound (Compound 7b) in 50.8% yield. Also isolated 703 mg of a Compound 7a/7b mixture in which was resubjected to the ketalization and equilibrium process to yield additional material. Compound 7b: NMR ($CDCl_3$) δ 0.790 (d, 3 H, J=7.2 Hz, C7α-$CH_3$), 0.963 (s, 3 H, C18-$CH_3$), 1.172(d, 3 H, C11β-$CH_3$), 3.186 (m, 5-lines, 1 H, C11α-CH), 3.661 (t, 1 H, J=8.7 Hz, C17α-CH) and 5.702 (s, 1 H, C4-CH).

H. Preparation of 7α,11β-Dimethyl-17β-hydroxy-4-estren-3-one (Compound 10)

Lithium wire (253 mg, 36.45 mmol), cut into small pieces, was added to redistilled (from sodium) ammonia (300 mL) and the mixture was stirred at ammonia reflux (−35° C.) for ½ hr. The mixture was chilled to −78° C. and a solution of the dienone (Compound 7b, 3.65 g 12.15 mmol) in THF (300 mL) and t-butanol (1.16 mL, 12.15 mmol) was added dropwise. Upon completion of the addition, the reaction was stirred for 15 min before any excess lithium was destroyed with the addition of isoprene (ca. 1.0 mL) and finally, quenched with the addition of solid ammonium chloride (15 g). The ammonia was evaporated under argon gas and the mixture was diluted with 0.1 N phosphate buffer, pH=7.0. The mixture was extracted with ether. The ether extracts were washed with water and brine, combined, and dried over sodium sulfate. Evaporation of the solvent gave 3.83 g of Compound 9 as a light yellow solid in quantitative yield. The material was homogeneous by TLC and was used without further purification in the following reaction. NMR ($CDCl_3$) δ 0.812 (d, 3 H, J=7.2 Hz, C7α-$CH_3$)m 0.877 (s, 3 H, C18-$CH_3$), 0.903 (d, 3 H, J=7.2 Hz, C11β-$CH_3$), 2.754 (br q, 2 H, C4-$CH_2$—), and 3.660 (t, 1H, J=8.8 Hz, C17α-CH).

The material prepared above was dissolved in methanol (400 mL) and 10% HCl (20 mL) was added and the mixture was heated at reflux for 3 hr. The solvent was evaporated and the residue was diluted with saturated sodium bicarbonate solution. The mixture was extracted with $CH_2Cl_2$. The methylene chloride extracts were washed with water and brine, combined and dried over sodium sulfate. Evaporation of the solvent gave 3.81 g of a stable foam. The material was chromatographed (10% acetone in $CH_2Cl_2$) to afford 3.54 g of Compound 10 in 96.5% yield. The material was recrystallized from ether/hexane to give 3.14 g of Compound 10 as fine white needles in 86% yield; m.p.=155–157° C. Analysis by reverse phase HPLC on a NovaPak $C_{18}$ column eluted with 50% aqueous $CH_3CN$ at a flow rate of 1 mL per min and at $\lambda$=240 nm indicated this material to have a purity in excess of 99% FTIR (KBr, diffuse reflectance): $V_{max}$ 3470, 2950, 1663 and 1622 $cm^{31\ 1}$. NMR (CDCl3) $\delta$ 0.770 (d, 3 H, J=7.2 Hz, C7$\alpha$-$CH_3$), 0.886 (s, 3 H, C18-$CH_3$), 1.075 (d, 3 H, J=7.2 Hz, C11$\beta$-$CH_3$), 3.626 (t, 1 H, J=8.7 Hz, C17$\alpha$-CH) and 5.849 (br s, 1 H, C4-CH). MS (EI) m/z relative intensity: 302 ($M^+$). Analysis calculated for $C_{20}H_{30}O_2$: C, 79.42; H, 10.00. Found: C, 79.18; H, 10.00.

H. Preparation of 7$\alpha$,11$\beta$-Dimethyl-17$\beta$-hydroxy-4-estren-3-one 17$\beta$-trans-4-n-butylcyclohexane carboxylate (Compound I)

Trans-4-n-Butylcyclohexanecarboxylic acid chloride (Compound 11, 2.25 g 110 mmol), dissolved in benzene (10 mL), was added to a solution of 7$\alpha$,11$\beta$-Dimethyl-17$\beta$-hydroxy-4-estren-3-one (Compound 10, 608 mg, 2 mmol) in a mixture of benzene (100 mL) and pyridine (5.0 mL). The mixture was stirred overnight at room temperature. The mixture was chilled in an ice bath and diluted with 1.0 N sodium hydroxide solution. The aqueous mixture was extracted with ether. The ether extracts were washed with 1.0 N sodium hydroxide solution (2x), water and brine. The combined organic extracts were dried over sodium sulfate and evaporation of the solvent gave 1.72 g of a semi-solid. Recrystallization of the material (Compound I) from hexanes gave 765 mg of white powder in 82% yield: m.p.=130–132° C. Analysis by reverse Phase HPLC on a NovaPak $C_{18}$ column eluted with $CH_3CN$ at a flow rate of 1.25 mL per minute and at $\lambda$=240 nm showed the Compound I to be pure greater than 99%. FTIR (KBr, diffuse reflectance) $V_{max}$ 2933, 1726, 1669 and 1621 $cm^{-1}$. MR (CDCl$_3$) $\delta$ 0.779 (d, 3 H, J=7.2 Hz, C7$\alpha$-$CH_3$), 0.886 (t, 3 H, n-butyl $CH_3$), 0.923 (s, 3 H, C18-$CH_3$), 1.057 (d, 3 H, J=7.2 Hz, C11$\beta$-$CH_3$), 4.545 (t, 1 H, J=8.7 Hz, C17$\alpha$-CH) and 5.848 (br s, 1 H, C4-CH). MS (EI) m/z relative intensity: 468 ($M^+$, 6.9), 358 (65.3), 302 (12.5), 284 (20.8), 269 (6.9), 259 (12.5), 174 (62.5), 159 (26.5), 147 (19.4), 139 (25.0), 119 (18.1), 110 (75.0), 105 (8.1), 97 (36.1), 83 (100), 69 (38.9) and 55 (58.3).

EXAMPLE 7

This example provides data on the androgenic potency of the undecanoate (CDB-4521A) relative to methyltestosterone (CDB-111 C) when administered via subcutaneous injection.

Immature (about 21-day-old) Sprague-Dawley rats were orchidectomized under anesthesia, and randomly assignee to groups of ten animals for each dose level of the active undergoing testing. Each active was dissolved in 10% ethanol/sesame oil and administered by subcutaneous injection each day for seven days beginning on the date of the orchidectomy. The animals were sacrificed 24 hours after the last dose, and the ventral prostate and seminal vesicles were excised, cleaned of fat and connective tissue, blotted on moist filter paper and weighed to the nearest 0.1 mg. See, e.g., Hershberger, L. et al, Myotrophic Activity of 19-nortestosterone And Other Steroids Determined By Modified Levator And Muscle Method, *Proc. Soc. Exptl. Bid. Med.* 83 175–180 (1953). Regression analysis was performed by conventional methods using a PROPHET data management system. See, e.g., Bliss, C., The Statistics of Bioassay (Academic Press, New York, 1952); Hollister, C., *Nucleic Acids Res.* 16 1873–75 (1988). Ventral prostate weight was used as the endpoint because it is the sensitive organ to androgenic stimulation.

Figure 13:
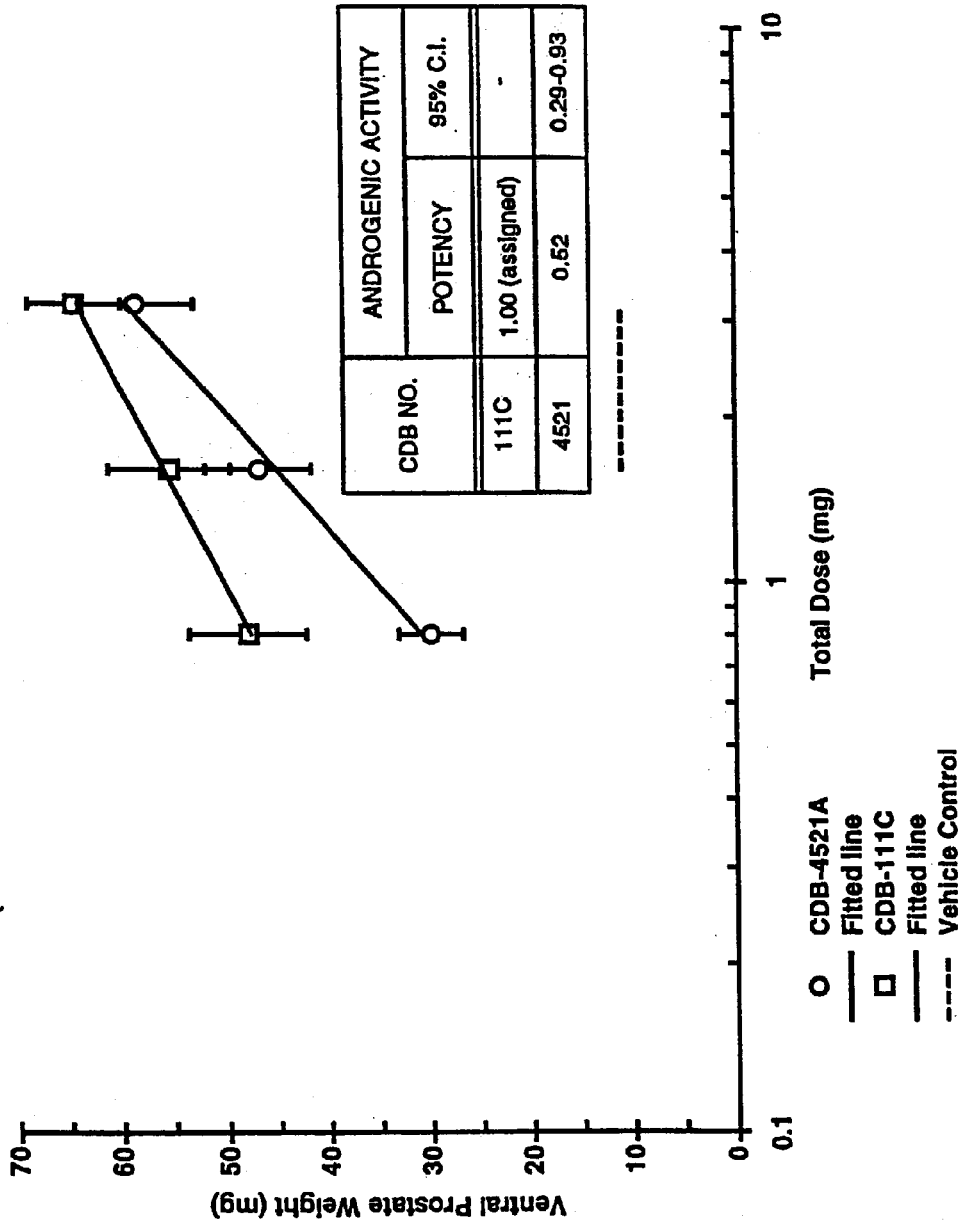
FIG. 13 is a graph comparing the androgenic potency of 7α,11β-dimethyl-17β-hydroxyestr-4-en-3-one 17-undecanoate and testosterone after subcutaneous injection.

The data obtained from this study is presented in graphic form in FIG. 13. This data indicates that the subcutaneous androgenic activity of the undecanoate (CDB-4521A) is about half that of testosterone (0.52 times, at a 95% confidence interval, 0.29–0.93) when administered in the oily carrier. This data was surprising when compared to the results obtained when the undecanoate was administered in an aqueous carrier.

EXAMPLE 8

This example provides data on the androgenic potency of the undecanoate (CDB-4521) and methyltestosterone (CDB-110) when orally administered in oily or aqueous carriers.

Immature (about 21-day-old) Sprague-Dawley rats were orchidectomized under anesthesia, and randomly assignee to groups of ten animals for each dose level of the active undergoing testing. Four dosage forms were prepared. The first two forms constituted a solution of each active in 10% ethanol/sesame oil. The third and fourth dosage forms constituted a suspension of each active in an aqueous carrier (as described in Example 2, supra). These dosage forms were then administered by gavage (oral) to separate animal groups each day for seven days beginning on the date of the orchidectomy. Each carrier was also administered (alone) to separate groups of animals as a control. The animals were sacrificed 24 hours after the last dose, and the ventral prostate and seminal vesicles were excised, cleaned of fat and connective tissue, blotted on moist filter paper and weighed to the nearest 0.1 mg. See, e.g., Hershberger, L. et al, Myotrophic Activity of 19-nortestosterone And Other Steroids Determined By Modified Levator And Muscle Method, *Proc. Soc. Exptl. Biol. Med.* 83 175–180 (1953). Regression analysis was performed by conventional methods using a PROPHET data management system. See, e.g., Bliss, C., The Statistics of Bioassay (Academic Press, New York, 1952); Hollister, C., *Nucleic Acids Res.* 16 1873–75 (1988). Ventral prostate weight was used as the endpoint because it is the sensitive organ to androgenic stimulation.

Figure 14:
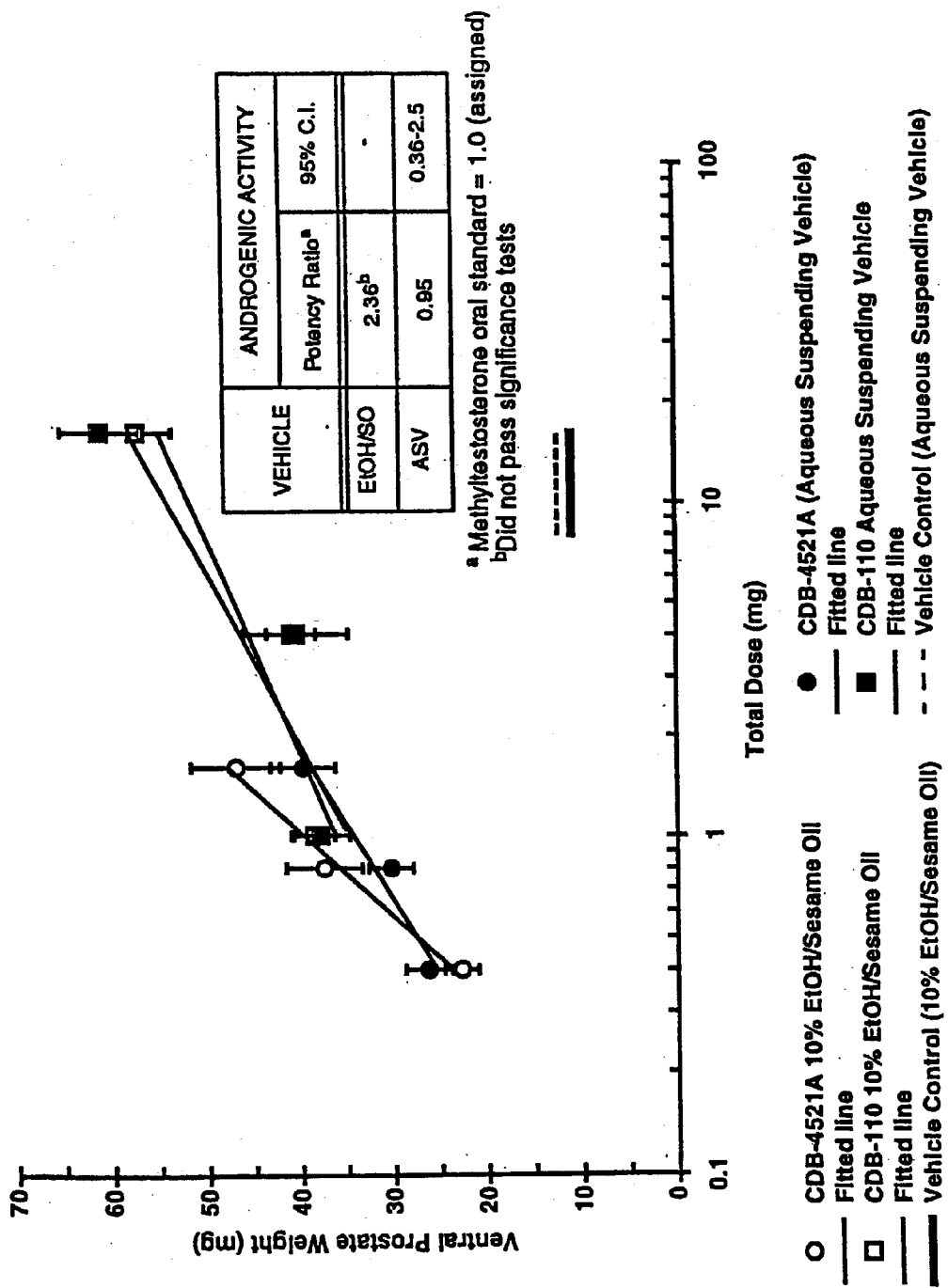
FIG. 14 is a graph comparing the androgenic potency of 7α,11β-dimethyl-17β-hydroxyestr-4-en-3-one 17-undecanoate and methyltestosterone after oral administration.

The data obtained from this study is presented in graphic form in FIGS. 14 and 4. This data indicates that the oral androgenic activity of the undecanoate (CDB-4521A) in the oily carrier is about 2 times (2.36 times, at a 95% confidence interval) as potent as methyltestosterone in the same oily carrier. In contrast, oral administration of the undecanoate in the aqueous carrier described in Example 2, supra, revealed a potency about the same (0.95 times, at a 95% confidence interval, 0.36–2.5) as that of methyltestosterone in the same aqueous carrier.

EXAMPLE 9

This example further illustrates the relative activity of 7$\alpha$,11$\beta$-dimethyl-17$\beta$-hydroxyestr-4-en-3-one 17-undecanoate (Compound II) compared to that of testosterone enanthate (CDB-112F) over relatively long periods of time.

Immature (about 21-day-old) Sprague-Dawley rats were orchidectomized under anesthesia, and randomly assignee to groups of 40 or more. Animals received a single subcutaneous injection of 0.6 mg of the undecanoate in 0.2 ml of an aqueous suspending carrier and/or oily carrier (10% ethanol/ 90% sesame oil containing 5 mg/ml chlorobutanol as a preservative, or ethyloleate) on the date of the orchidectomy. The enanthate ester was formulated using the 10% ethanol/ sesame oil or ethyloleate carrier as a first standard, with the 10% ethanol/sesame oil carrier used as a second standard.

In this example, the carrier used to provide the aqueous suspension was formulated as follows: 1 g benzyl alcohol, 0.5 g sodium carboxylethyl cellulose 50, 0.376 g disodium hydrogen phosphate dihydrate, 1.495 g sodium dihydrogen phosphate dihydrate, with water for injection (WFI) being added to bring volume of the carrier up to 100 ml.

Five animals from each group were sacrificed at weekly or biweekly intervals, and the ventral prostate and seminal vesicles were excised, cleaned of fat and connective tissue, blotted on moist filter paper and weighed to the nearest 0.1 mg.

Ventral prostate weight was used as the endpoint because it is the sensitive organ to androgenic stimulation. Regression analysis was performed by conventional methods using the PROPHET data management system previously identified.

Figure 15:
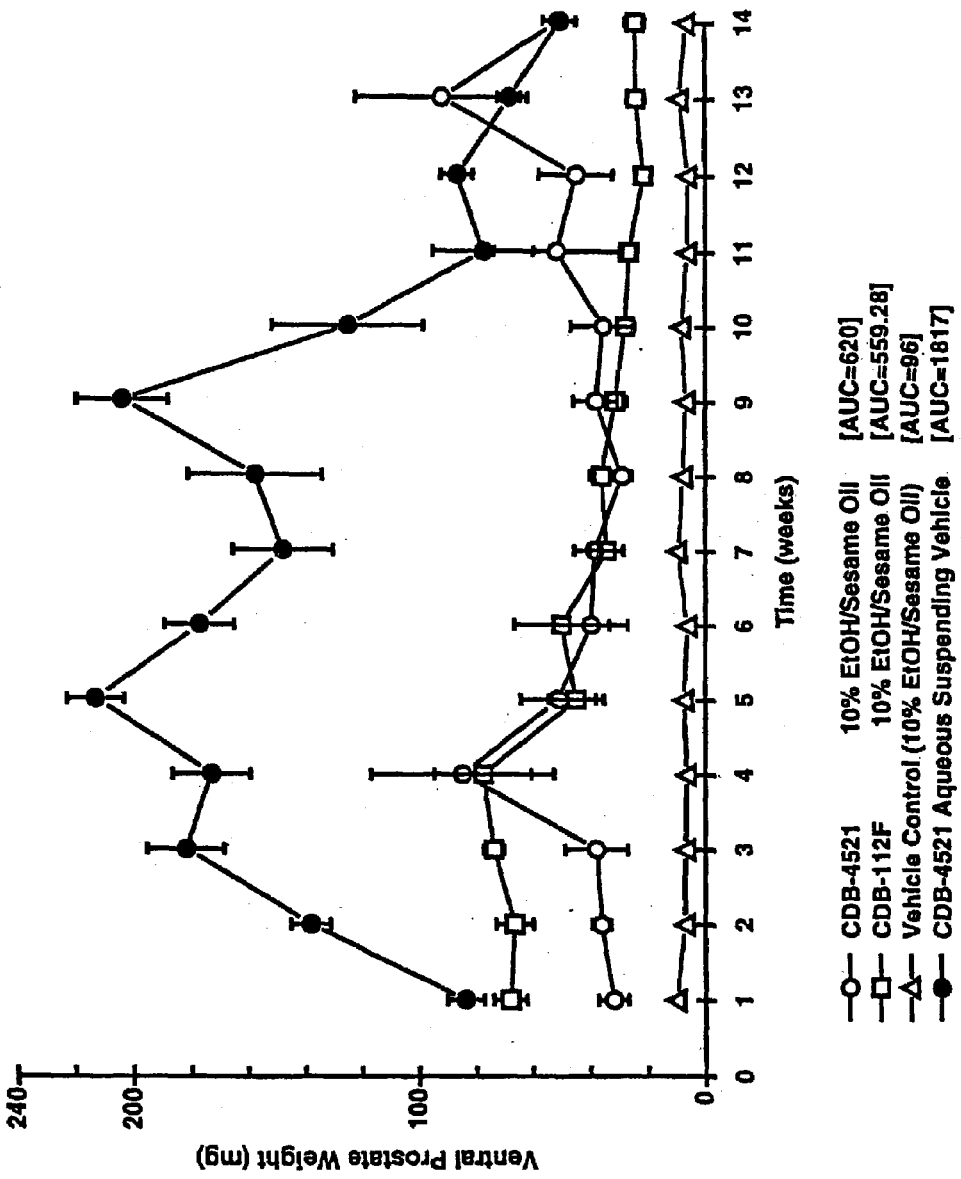
FIG. 15 is a graph comparing the duration of activity of 7α,11β-dimethyl-17β-hydroxyestr-4-en-3-one 17-undecanoate and that of testosterone enanthate (CDB-112F) after subcutaneous injection.

FIG. 15 is a graphic representation of the androgenic assays of the actives. Each data point represents the mean (n=10) and standard error of the mean (SEM) for each prostate weight for each formulation level.

More specifically, FIG. 15 is a graph of the ventral prostate weights at weekly intervals over a 10 week period after the subcutaneous administration of the undecanoate (CDB-4521) in both oily and aqueous carriers, testosterone enanthate (CDB-112F) in an oily carrier, and an oily carrier (10% ethanol/sesame oil) alone. The undecanoate in the aqueous vehicle exhibited the most dramatic increase and maintenance of ventral prostate weight. The area under the curve (AUC, calculated by the trapezoidal rule), was about 3 times greater for the undecanoate (1817 mg-weeks) than for testosterone enanthate in the oily carrier (AUC 559 mg-weeks).

This experiment highlights the significance of the ability to provide the undecanoate in the form of an aqueous suspension, which provides unexpected and desirable long-term androgenic activity. This experiment also underscores the importance of the stereoconfiguration of the $C_{11}$ substituent.

EXAMPLE 10

This example describes a preferred process for synthesizing 7α,11β-dimethyl-17β-hydroxyestr-4-en-3-one 17-undecanoate (Compound II). Reference may be made to FIG. 16.

The synthesis of Compound 10 as described in Example 6 was completed. Thereafter, the undecanoate was prepared by treatment of Compound 10 with undecanoyl chloride in pyridine to provide Compound II as a white powder, in good yield.

A solution of 7α,11β-dimethyl-17β-hydroxyestr-4-en-3-one (Compound 10, 252 mg, 0.83 mmol) in a mixture of benzene (20 mL) and pyridine (2.0 mL) was treated with undecanoyl chloride (Compound 12, 500 mg, 2.44 mmol). The mixture was stirred at room temperature overnight. The mixture was then chilled in an ice bath and diluted with cold 0.1 N sodium hydroxide solution. The resulting aqueous mixture was extracted with ether. The ether extracts were washed with water and brine, combined and dried over sodium sulfate. Evaporation of the solvent gave 525 mg of an oil. The material was chromatographed using 10% acetone/$CH_2Cl_2$ to yield 398 mg of an oil. The material was recrystallized from cold pentane to afford 369.2 mg of Compound II as a white powder in 94% yield; m.p.=62–64° C. Analysis by reverse Phase HPLC on a NovaPak $C_{18}$ Column eluted with $CH_3CN$ at a flow rate of 1.0 mL per mm and at λ=240 nm showed Compound II to have a purity of at least 99.9%. FTIR (KBr, diffuse reflectance): $V_{max}$ 2914, 1733, 1678 and 1628 $cm^{-1}$. $^1$HNMR ($CDCl_3$) δ 0.782 (d, 3 H, J=7.2 Hz, C7α-$CH_3$), 0.880 (t, 3 H, J=9 Hz, —$(CH_2)_9$C$H_3$,), 0.922 (s, 3 H, C18-$CH_3$), 1.058 (d, 3 H, J=7.2 Hz, C11β-$CH_3$), 4.565 (t, 1 H, J=8.4 Hz, C17α-CH) and 5.849 (s, 1 H, C4-CH=). MS (EI) m/z (relative intensity): 470 ($M^+$, 100), 302 (60), 284 (78), 259 (67), 175(89), 110 (69) and 55(96). Analysis Calculated for $C_{31}H_{50}O_3$: C, 79.10; H, 10.70. Found: C, 79.33; H, 10.91.

EXAMPLE 11

This example describes a preferred process for synthesizing 7α,11β-dimethyl-17β-hydroxyestra-4,14-dien-3 -one, 7α,11β-dimethyl-17β-hydroxyestra-4,14-dien-3-one 17-undecanoate, and 7α,11β-dimethyl-17βhydroxyestra-4,14-dien-3-one 17β-4-n-butylcyclohexanecarboxylate.

A. Preparing Compound 102 From Compound 101

Under a nitrogen flush, a pyridine (250 mL)/acetic anhydride (25 mL) solution of Compound 1 (4.44 g, 14.7 mmol) was stirred for 24 hours. The solvent was evaporated in vacuo and residual pyridine was removed by co-evaporation three times with heptane to afford 5.05 g of the 17-acetate as a white powder in 100% yield. NMR ($CDCl_3$) δ 0.777 (d, 3 H, J=7.2 Hz, C7α-$CH_3$), 0.925 (s, 3 H, C18-$CH_3$), 1.060 (d,3 H, J=7.5 Hz, C11β-$CH_3$), 2.048 (s, 3 H, C17β-Oac), 4.554 (t, 1 H, J=8.1 Hz, C17α-H) and 5.489 (s, 1 H, C4-CH=).

An acetonitrile (180 mL) solution of the ketoacetate (5.0 g, 14.50 mmol) was treated with lithium bromide) (1.26 g, 14.50 mmol) and copper (II) bromide (6.48 g, 29.00 mmol). The mixture was stirred at room temperature for two hours and subsequently chilled in an ice bath. The reaction was diluted with cold water and extracted with ethyl acetate. The ethyl acetate extracts were washed with water, brine, combined and dried over sodium sulfate. Evaporation of the solvent gave 5.91 g of the crude phenol acetate. Chromatography, eluting with 2% acetone in dichlormethane, gave 3.96 g of the pure phenol acetate as a white solid in 79% yield. NMR ($CDCl_3$) δ 0.812 (d, 3 J, J=7.2 Hz, C17α-$CH_3$), 0.843 (d, 3 H, J=7.3 Hz, C11β-$CH_3$), 0.936 (s, 3H, C18-$CH_3$), 2.064 (s, 3H, C17α-Oac), 4,648 (t, 1 H, J=8.03 Hz, C17α-H), 6.521 (d, 1 H, J=3 Hz, C4-aromatic CH—), 6.637, (dd, 1 H, J=8.4 Hz, J'=3 Hz, C2-aromatic CH—) and 7.032 (d, 1 H, J=8.4 Hz, C1-aromatic CH—)

This material (3.96 g, 11.48 mmol) was dissolved in methanol (400 ml) and treated with excess potassium hydroxide (2.72 g, 48.57 mmol in 40 mL of water). The mixture was heated at reflux for two hours and methanol was evaporated in vacuo. The materials was taken up in water and pH was adjusted to a level of 1–2 with the addition of HCl. The aqueous mixture was extracted with dichloromethane. The organic extracts were washed with water and brine, combined and dried over sodium sulfate. Evaporation of the solvent gave 3.27 g of the diol (Compound 102) as a white solid in 95% yield. FTIR (KBr, diffuse reflectance): $V_{max}$ 3353, 3106, 2894, 1614, 1578, 1497 and 1243 $cm^{-1}$. NMR ($CDCl_3$+tr. $D_4MeOH$) δ 0.804 (d, 3 H, J=7.2

Hz, C7α-CH$_3$), 0.856 (d, 3 H, J=7.3 Hz, C11β-CH$_3$), 0.888 (s, 3 H, C-18- CH$_3$), 3.712 (t, 1 H, J=8.03 Hz, C17α-H), 6.521 (d, 1 H, J=3 Hz, C4-aromatic CH—), 6.636 (dd, 1 H, J=8.4 Hz, J'–3 Hz, C2 –aromatic CH—) and 7.011(d,1 H, J=8.4 Hz, C1-aromatic CH—).

B. Preparation of Compound 103

A THF (200 mL) solution of Compound 102 (3.27 g, 10.88 mmol) was treated with lithium hydroxide (685 mg, 16.33 mmol), followed by the addition of dimethyl sulfate (1.14 mL, 11.97 mmol) and the mixture was heated at reflux for 2 hours. The mixture was cooled to room temperature, filtered through Celite and the filtrate was evaporated. The residue was taken up in ether and washed with water and brine. The ether solution was dried over sodium sulfate. Evaporation of the solvent gave 3.35 g of the methyl ether, Compound 103. The crude material was dissolved in acetone (150 mL) and chilled in an ice bath. The cold solution was treated dropwise with Jones reagent until the orange color of Cr(IV) persisted. The mixture was diluted with cold water and extracted with ether. The ether extracts were washed with water, brine, combined and dried over sodium sulfate. Evaporation of the solvent gave 3.28 g of the ketone as a white solid in 96% yield. Recrystallization of a small sample from ether/hexane provided an analytical sample with a melting point between 121–123° C. FTIR (KBr, diffuse reflectance): V$_{max}$ 2962, 1736, 1612 m 1573 m 1500 and 1048 cm$_{-1}$. NMR (CDCl$_3$) δ 0.847 (d, 6 H, C7α-CH$_3$), C11β-CH$_3$), 1.061 (s, 3 H, C18-CH$_3$), 3.077 (s, 3 H, C3-OCH$_3$), 6.597 (d, 1 H, J=3 Hz, C4-aromatic CH—), 6.730 (dd, 1 H, J=8.4 Hz, J'=3 Hz, C2 -aromatic CH—) and 7.093 (d, 1 H, J=8.4 Hz, C1-aromatic CH—). MS (EI) m/z (relative intensity: 312 (M$^+$), 213, 200, 185, 174 and 159. Analysis calculated for C$_{21}$H$_{28}$O$_2$: C, 80.70; H, 9.00. Found: C, 81.00; H, 9.20.

C. Preparation of Compound 104

A THF (10 mL) solution of Compound 103 (520 mg, 1.66 mmol) was added dropwise over 10–12 minutes to a 2.0 M lithium diisopropylamide solution (1.66 mL, 3.33 mmol) chilled to –78° C. for 15 minutes, before triethyl amine (0.62 mL, 4.40 mmol) was added, followed by the addition of chlorotrimethylsilane in THF (1.0 M) (3.33 mL, 3.33 mmol). The reaction mixture was allowed to come to room temperature for 25 minutes before being diluted with cold saturated bicarbonate solution. The mixture was extracted with Ethyl Acetate. The ethyl acetate extracts were washed with water, brine, combine and dried over sodium sulfate. Evaporation of the solvent gave 632 mg of a yellow oil in 99% yield that was homogeneous by Thin Layer Chromatography (TLC) and used without further purification in the subsequent reaction.

This enol trimethylsilyl ether was dissolved in dichloromethane (12 mL) and acetonitrile (4.0 mL) and palladium acetate (395 mg, 1.76 mmol) was added. The mixture was stirred at 35–40°C. for three hours. The solvent was evaporated in vacuo and the residue was chromatographed, eluting with 2% acetone in dichloromethane, to afford 352 mg of the enone (Compound 104) as a light yellow solid in 68% yield along with the recovered of 108 mg of the ketone, Compound 103. Recrystallization of a small sample of Compound 104 from ether/hexanes provided an analytical sample with a melting point of 135–136° C. FTIR (KBr, diffuse reflectance): V$_{max}$ 2989, 2958, 1707, 1609, 1573 and 1497 cm$^{-1}$. NMR (CDCl$_3$) δ 0.917 (d, 3 H, J=7.2 Hz, C7α-CH$_3$), 0.984 (d, 3H, J=7.3 Hz, C11β-CH$_3$), 1.236 (s, 3 H, C-18-CH$_3$), 3.781 (s, 3 H, C3-OCH$_3$), 6.058 (m, 1 H, C16-CH=), 6.611 (d, 1 H, J=3 Hz, C4=-aromatic CH—), 6,735 (dd, 1 H, J=8.4 Hz, J'=3 Hz, C2-aromatic Ch-) 7.098 (d, 1 H, J=8.4 Hz, C1-aromatic CH—) and 7.585 (m,1H, C15-CH=). MS (EI) m/z (relative intensity) 310 (M+), 295, 282, 267, 253, 239, 202, 189, 174 and 159. Analysis calculated for C$_{21}$H$_{26}$O$_2$: C, 81.30; H, 8.40 Found: C, 81.13; H, 8.55.

D. Preparation of Compound 105

The enone (Compound 104) (1.41 g, 4.54 mmol) was dissolved in a 1:1 mixture of isopropenyl acetate and acetic anhydride (100 mL) and p-toluenesulfonic acid monohydrate (86 mg, 0.45 mmol) was added. The mixture was heated at reflux for four hours. The mixture was cooled to room temperature, poured into ice water and stirred for one hour. The mixture was extracted with ether. The ether extracts were washed with saturated sodium bicarbonate solution two times, water and brine. The combined ether extracts were dried over sodium sulfate and evaporation of the solvent gave 1.78 g of a crude Compound 105. Chromatography, eluting with 2% acetone in dichloromethane, afforded 1.34 g of the dienolacetate (Compound 105) as a light yellow oil in 84 % yield along with the recovery of 0.12 g of the enone Compound 104. The actual conversion yield was 92%. NMR (CDCl$_3$) δ 0.974 (d, 3 H, J=7.2 Hz, C7α-CH$_3$), 1.023 (d, 3 H, J=7.3 Hz, C11β-CH$_3$), 1.215 (s, 3 H, C18-CH$_3$), 2.225 (s, 3 H, C17-OAc), 3.781 (s, 3 H, C3-OCH$_3$), 5.926 and 6.096 (d, 2 H, J=2.25 Hz, C15 and C16-CH=), 6.616 (d, 1 H, J=3 Hz, C4-aromatic CH—), 6,730 (dd, 1 H, J=8.4 Hz, J'=3 Hz, C2=aromatic CH—) and 7.098 (d, 1 H, J=8.4 Hz, C1-aromatic CH—).

E. Preparation of Compound 106

The dienolacetate Compound 105 (1.59g, 4.51 mmo) was dissolved in ethanol (70 mL) and chilled in an ice-bath. A 23% aqueous ethanol (70 mL) of sodium borohydride (640 mg, 16.92 mmol) was chilled to 0° C. and added to the solution of Compound 105. The mixture was allowed to warm to room temperature and stirred overnight. Acetic acid was added to the reaction mixture to a pH level of 6 and the ethanol was evaporated in vacuo. The residue was diluted with water and the mixture was extracted with diclorormethane. The organic extracts were washed with water and brine, combined and dried over sodium sulfate. Evaporation of the solvent gave 1.42 g of Compound 106 as white foam in 89% yield. This product was homogeneous by TLC and used in the subsequent reaction without further purification. NMR (CDCl$_3$) δ 0.894 (m, 3-lines, 3 H, C7α-CH$_3$ & C11β-CH$_3$), 1.078 (s, 3 H, C18-CH$_3$), 3.778 (s, 3 H, C3-OCH$_3$), 4.024 (t, 1 H, J=8.2 Hz, C17α-CH), 5.177 (br s, 1 H, C15-CH=), 6.600 (d, 1 H, J=3 Hz, C4-aromatic CH—), 6.732 (dd, 1 H, J=8.4 Hz, J'=3 Hz, C2-aromatic CH—) and 7.167 (d, 1 H, J=8.4 Hz, C1-aromatic CH—).

F. Preparation of Compound III

A THF (50 mL)/t-butanol (50 mL) solution of Compound 106 (1.42 g, 4.54 mmol) was added to anhydrous liquid ammonia (distilled from sodium) at –78° C. With vigorous stirring, lithium wire (630 mg, 90.82 mmol), cut into small pieces, was added. The resulting blue mixture was stirred at ammonia reflux for three hours. The reaction mixture was chilled to –78° C. and quenched through the addition of methanol. The ammonia was evaporation under a stream of nitrogen and then diluted with water. The aqueous mixture was extracted with ether. The ether extracts were washed with water and brine, combined and dried over sodium sulfate. Evaporation of the solvent gave 1.45 g of the 1,4 dihydro derivative as a white powder in >100% yield. This crude materials was dissolved in methanol (250 mL) and treated with 10% HCl (10 Ml) and the mixture was diluted with saturated with NaHCO$_3$. The aqueous mixture was extracted with dichloromethane. The organic extracts were washed with water, brine, combined, dried over Na$_2$SO$_4$. Evaporation of the solvent gave 1.35 g of a stable foam. This crude product was subjected to chromatography, eluting with 9% acetone in dichloromethane, to afford 0.95 g of Compound III as a white powder in 70% yield and the recovery of 0.330 g of the 5(10)-en-3-one. A small sample of Compound III was recrystallized from ether/hexanes to afford an analytical sample with melting point of 149–151° C. FTIR (KBr, diffuse reflectance): V$_{max}$ 3477, 2971, 2897, 1655 and 1612 cm$_{-1}$. NMR (CDCl$_3$) δ 0.837 (d, 3 H, C7α-CH$_3$), 1.063 (s, 3 H, C18-CH$_3$), 1.135 (d, 3H, J=7.2 Hz, C11β-CH$_3$), 3.895 (t, 1 H, J=8.7 Hz, C17α-CH), 5.141 (br, s 1 H, C15-CH=), 5.874 (br s, 1 H, C4-CH=). MS (EI) m/z (relative intensity): 300 (M$^+$, 91), 285 (19), 256 (36), 214 (25), 190 (33), 173 (62), 163 (55), 161 (42), 147 (74), 145 (45), 136 (45), 119 (74), 107 (57), 105 (70), 93 (43), 91 (100), 79 (66), 77 (74), 67 (43) and 55 (83). Analysis calculated for C$_{20}$H$_{28}$O$_2$: C, 80.00; H, 9.40. Found: C, 79.77; H, 9.48.

G. Preparation of Compound IV

A benzene (8.0 mL)/pyridine solution (1.0 mL) of the alcohol Compound 107 (162 mg, 0.54 mmol) was treated with an excess undecanoyl chloride (500 mg, 2.41 mmol) and the mixture was stirred at room temperature for two hours. The mixture was chilled in an ice bath and diluted with saturated sodium bicarbonate solution. The aqueous mixture was extracted with ether. The ether extracts were washed with water and brine. The combined ether extracts were dried over sodium sulfate and evaporation of the solvent gave 620 mg of an oil containing undecanoic acid and Compound IV. The crude material was subjected to chromatography, eluting with 1% acetone in dichloromethane to give 251 mg of the ester of Compound IV in 99% yield. This material exists as a low melting wax and would not crystallize from a variety of solvents. FTIR (KBr, diffuse reflectance): V$_{max}$, 2925, 2853, 1737, 1673 and 1466 cm−1. NMR (CDCl$_3$) δ 0.865 (d, 3 H, J=7.2 Hz, C7 α- CH$_3$), 1.079 (s, 3 H, C18-CH$_3$), 1.158 (d, 3 H, J=7.2 Hz, C11β-CH$_3$), 4.889 (t, 1 H, J=8.4 Hz, C17 α-CH), 5.161 (br s, 1 H, C15-CH=), and 5.873 (s, 1 H, C4-CH=). MS (EI) m/z (relative intensity): 468.7 (M+, 14.5), 283 (27), 282 (100), 189 (17), 173 (15), 147 (21), 119 917), 105 (17) 93, 917), 69 (17) and 57 (27). Analysis calculated for C$_{31}$H$_{48}$O$_2$•1; 4H$_2$O: C, 78.70; H, 10.30. Found: C, 78.78; H, 10.36.

H. Preparation of Compound V

A benzene (8.0 mL)/pyridine (1.0 mL) solution of Compound 107 (129 mg, 0.43 mmol) was treated with trans-4-n-butylcyclohexanecarboxylic acid chloride (349 mg, 1.72 mmol) and stirred at room temperature for two hours. The mixture was chilled in an ice bath and diluted with saturated sodium bicarbonate solution. The aqueous mixture was extracted with ether. The ether extracts were washed with water and brine, combined and dried over sodium sulfate. Evaporation of the solvent gave 480 mg of an oil containing trans-4-n-butylcyclohexanecarboxylic acid and Compound V. The crude material was subjected to chromatography, eluting with 5% acetone in dichloromethane, to give 189 mg of the ester Compound V as a glass with 95% yield. The material was recrystallized from cold pentane to afford 120 mg of pure Compund 9 as a white powder in 60% yield with a melting point of 84–85° C. fTIR (KBr, diffuse reflectance): V$_{max}$2929, 2854, 1673, 1613 and 1453 cm$^{-1.}$ NMR (CDCl$_3$) δ 0.867 (d, 3H, J=0.2 Hz, C7 α- CH$_3$)), 1.076 (s, 3 H, C18-CH$_3$) 1.158 (d, 3 H, J=7.2 Hz, C11β-CH$_3$), 4.873 (t, 1 H, J=8.4 Hz, C17α-CH), 5.161 (br s, 1 H C15-CH=), and 5,873 (s, 1 H, C4-CH=). MS (EI) m/z (relative intensity): 466 (M$^+$, 10), 283 (17), 282 (100), 190 (17), 172 927), 157 (19), 147 (38), 119 (17), 105 (17), 93(17), 83 (50), 69 (38) and 55 (46). Analysis calculated for C$_{31}$H$_{46}$O$_3$: C, 79.83; H, 9.87. Found: C, 79.91; H, 9.96.

EXAMPLE 12

This example provides data on the androgenic potency of Compounds IV and V when administered orally.

Immature (about 21 day old) Sprague male rats were orchidectomized under anesthesia, and randomly assignee to groups often animals for each dose level of the active undergoing testing. Animals were maintained under standard conditions of housing and had free access to food and water. Illumination was controlled for 14 hour periods of light and 10 hours of darkness. Each active was dissolved in 10% ethanol/sesame oil and administered by gavage (oral) each day for seven days beginning on the date of the orchidectomy. The animals were sacrificed 24 hours after the last dose, and the ventral prostate and seminal vesicles were excised, cleaned of fat and connective tissue, blotted on moist filter paper and weighed to the nearest 0.1 mg. See, e.g., Hershberger, L. et al, Myotrophic Activity of 19-nortestosterone And Other Steroids Determined By Modified Levator And Muscle Method, *Proc. Soc. Exptl. Biol. Med.* 83 175–180 (1953). Regression analysis was performed by conventional methods using a PROPHET data management system. See, e.g., Bliss, C., The Statistics of Bioassay (Academic Press, New York, 1952); Hollister, C., *Nucleic Acids Res.* 16 1873–75 (1988). Ventral prostate weight was used as the endpoint because it is the sensitive organ to androgenic stimulation.

Figure 20:
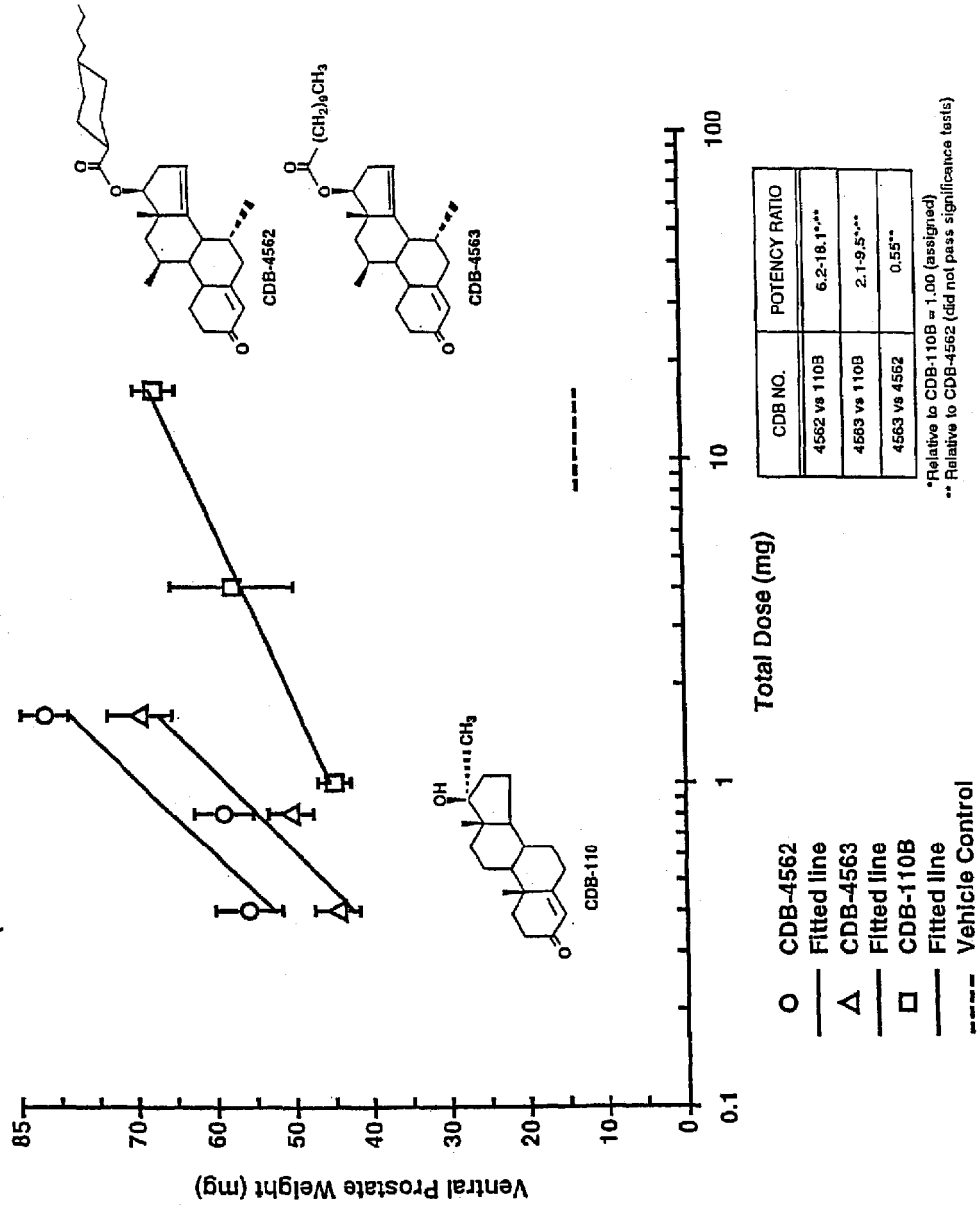
FIG. 20 is a graph comparing the androgenic potency of 7α,11β-dimethyl-17β-hydroxyestra-4,14-dien-3-one 17-undecanoate, 7α,11β-dimethyl-17β-hydroxyestra-4,14-dien-3-one 17β-4-n-butylcyclohexanecarboxylate, and testosterone after oral administration.

As displayed in FIG. 20, about six to about eighteen times the oral activity of the standard methyltestosterone were exhibited in testing performed on Compound V. Compound IV test results exhibited about two to about nine times the oral activity of methyltestosterone. These findings were unexpected due to the relative inactivity of testosterone and its esters on oral administration, yet it is believed that this may be explained, in part, due to the protections that the ester receives from degradation in the gastrointestinal tract and/or rapid metabolism by the liver. It is also conceivable that the lipophilic nature of Compound V permits absorption into the thoracic lymph thus avoiding direct entrance into the portal system and "first-pass" metabolism in the liver.

EXAMPLE 13

This example provides data on the androgenic potency of Compounds IV and V when administered parenterally (by subcutaneous injection).

Immature (about 22-day-old) Sprague-Dawley male rats were orchidectomized under anesthesia, and randomly assignee to groups of ten animals for each dose level of the active undergoing testing. The animals were maintained under standard conditions of housing and had free access to food and water. Illumination was controlled for 14 hour periods of light and 10 hours of darkness.

Each active was administered by subcutaneous injection of 0.6 mg of test material in aqueous suspending vehicle (ASV) and/or an oily vehicle (10% ethanol/sesame oil) on the day of surgery. Testosterone enanthate in sesame oil was used as a standard. The ventral prostate and seminal vesicles were excised, cleaned of fat and connective tissue, blotted on moist filter paper and weighed to the nearest 0.1 mg. Regression analysis was performed by conventional methods using a PROPHET data management system. Ventral prostate weight was used as the endpoint because it is the sensitive organ to androgenic stimulation.

Figure 21:
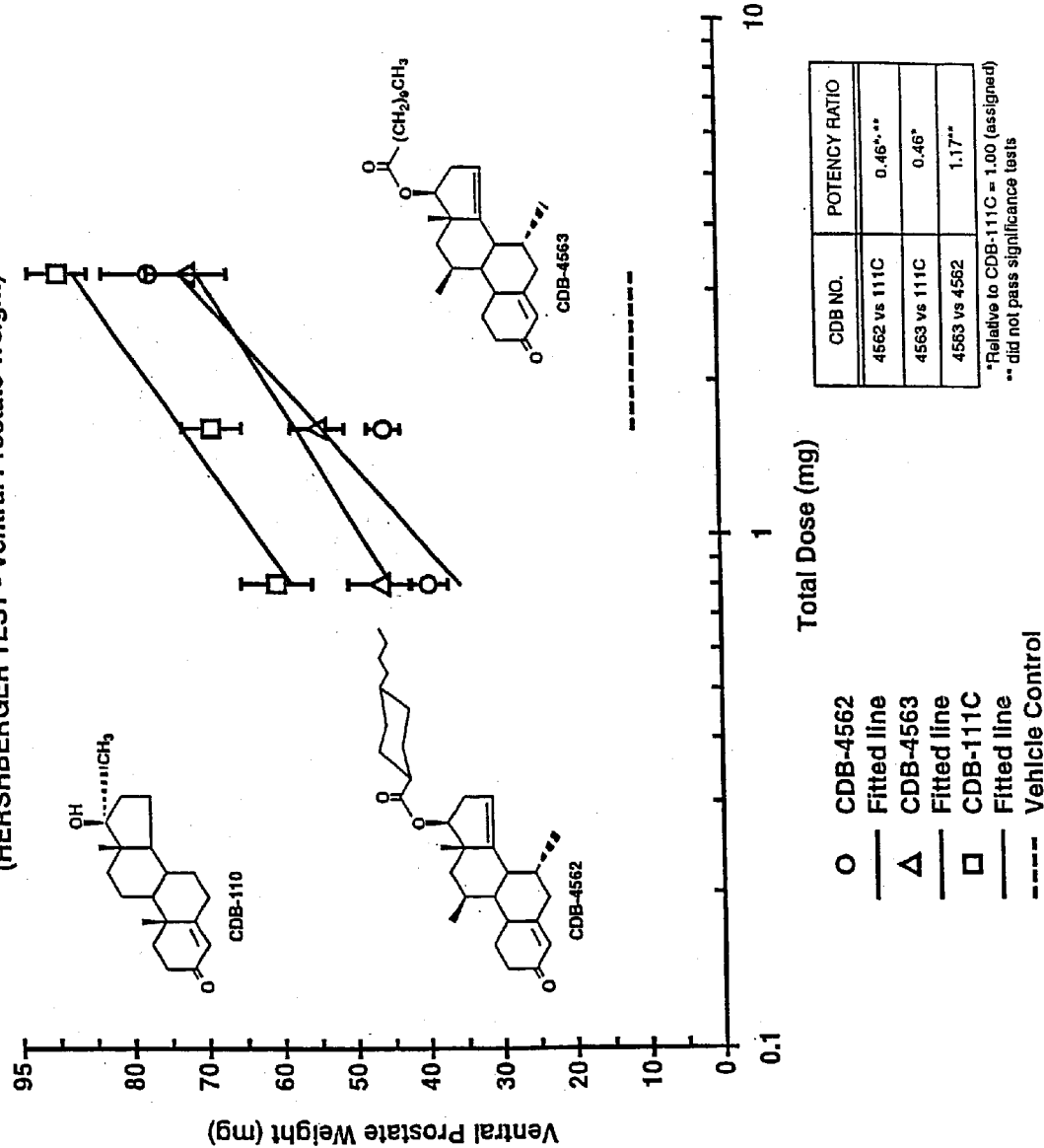
FIG. 21 is a graph comparing the androgenic potency of 7α,11β-dimethyl-17β-hydroxyestra-4,14-dien-3-one 17-undecanoate, 7α,11β-dimethyl-17β-hydroxyestra-4,14-dien-3-one 17β-4-n-butylcyclohexanecarboxylate, and testosterone after subcutaneous injection.

As seen in FIG. 21, both esters exhibited about one-half (0.46) times the activity of methyltestosterone following subcutaneous administration. This weak activity was surprising given the potent long-action action following a single subcutaneous injection. The lack of potent subcutaneous activity likely reflects the slow release of the drug from the injection site over the 7-day administration period.

EXAMPLE 14

This example further illustrates the relative activity of 17 esters of 7α,11β-dimethyl-17β-hydroxyestra-4,14-dien-3-one (i.e., 7α,11β-dimethyl-17β-hydroxyestra-4,14-dien-3-one 17-undecanoate (Compound IV; CDB-4563) and 7α,11β-dimethyl-17βhydroxyestra-4,14-dien-3-one 17β-4-n-butylcyclohexanecarboxylate (Compound V; CDB-4562) compared to that of testosterone enanthate (CDB-112F) and other androgens (i.e., testoterone bucyclate, CDB-1781a at 1 mg dosage; Dimethandrolone undecanoate, CDB-4521; and Dimethandrolone bucyclate, CDB-4386A) over relatively long periods of time.

Immature (about 21-day-old) Sprague-Dawley rats were orchidectomized under anesthesia, and randomly assignee to groups of 40 or more. Animals received a single subcutaneous injection of 0.6 mg of an active (with the exception of testosterone bucyclate of which 1 mg was administered) in 0.2 ml of an aqueous suspending carrier and/or oily carrier (10% ethanol/90% sesame oil containing 5 mg/ml chlorobutanol as a preservative, or ethyloleate) on the date of the orchidectomy. The enanthate ester was formulated using the 10% ethanol/sesame oil or ethyloleate carrier as a first standard, with the 10% ethanol/sesame oil carrier used as a second standard.

In this example, the carrier used to provide the aqueous suspension was formulated as follows: 1 g benzyl alcohol, 0.5 g sodium carboxylethyl cellulose 50, 0.376 g disodium hydrogen phosphate dihydrate, 1.495 g sodium dihydrogen phosphate dihydrate, with water for injection (WFI) being added to bring volume of the carrier up to 100 ml.

Five animals from each group were sacrificed at weekly or biweekly intervals, and the ventral prostate and seminal vesicles were excised, cleaned of fat and connective tissue, blotted on moist filter paper and weighed to the nearest 0.1 mg.

Ventral prostate weight was used as the endpoint because it is the sensitive organ to androgenic stimulation. Regression analysis was performed by conventional methods using the PROPHET data management system previously identified.

Figure 22:
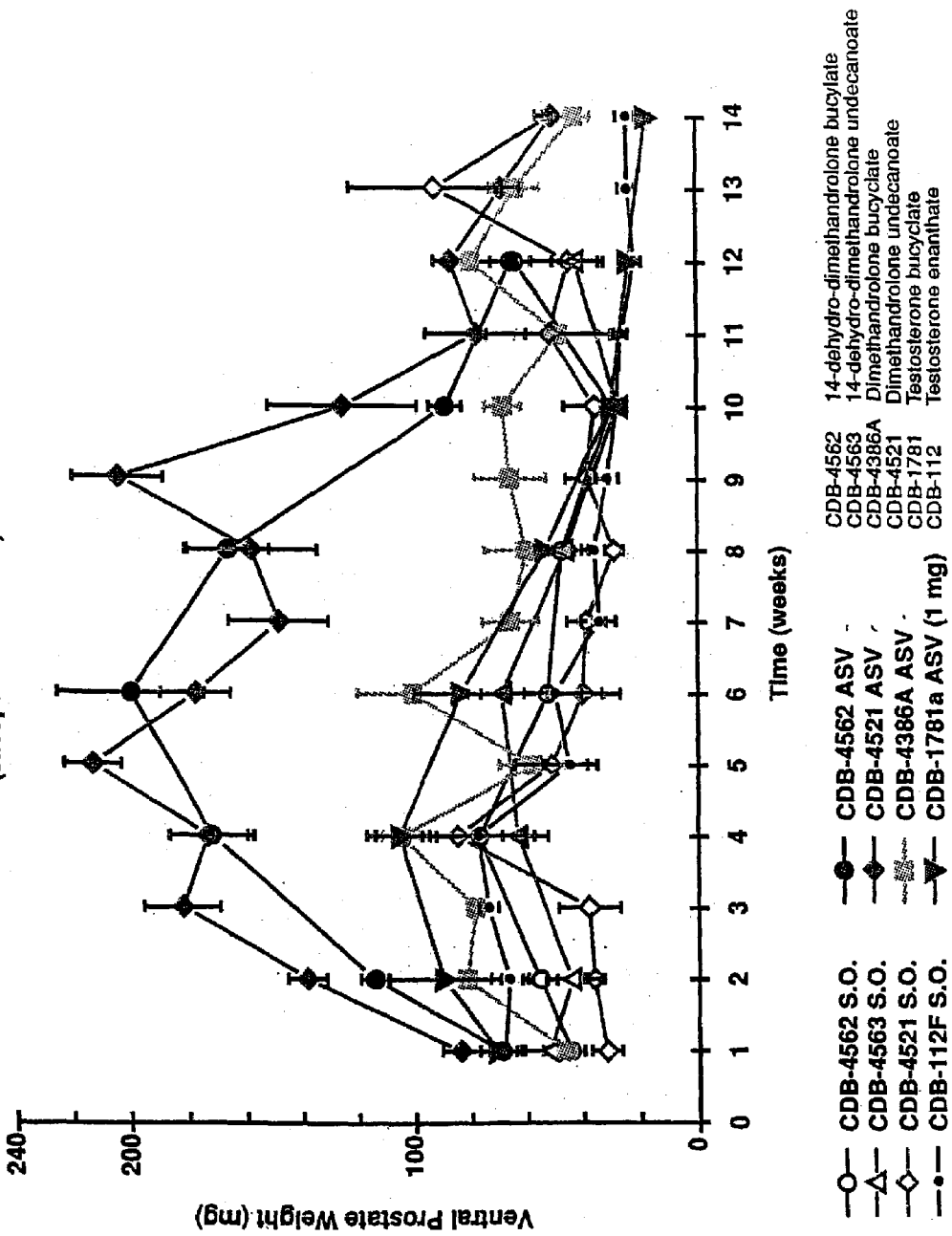
FIG. 22 is a graph comparing the duration of activity of 7α,11β-dimethyl-17β-hydroxyestra-4,14-dien-3-one 17-undecanoate, 7α,11β-dimethyl-17β-hydroxyestra-4,14-dien-3-one 17β-4-n-butylcyclohexanecarboxylate and that of other compounds after subcutaneous injection.

FIG. 22 is a graphic representation of the androgenic assays of the actives. Each data point represents the mean (n=10) and standard error of the mean (SEM) for each prostate weight for each formulation level.

More specifically, FIG. 22 is a graph of the ventral prostate weights at weekly intervals over a 12 week period after the subcutaneous administration of the actives in the carriers (as indicated in FIG. 22). CDB-4521 and CDB-4562 in the aqueous vehicle exhibited the most dramatic increases and maintenance of ventral prostate weight. The area under the curve (AUC, calculated by the trapezoidal rule), was about 3 times greater for CDB-4562 in the aqueous vehicle (AUC 1521 mg-weeks), than for testosterone enanthate in the oily carrier (AUC 513 mg-weeks). The aqueous vehicle control exhibited an AUC of 81 mg-weeks. This experiment highlights the significance of the ability to provide 7α,11β-dimethyl-17βhydroxyestra-4,14-dien-3-one 17β-4-n-butyl-cyclohexanecarboxylate (Compound V; CDB-4562) in the form of an aqueous suspension, which provides unexpected and desirable long-term androgenic activity. This experiment also underscores the importance of the stereoconfiguration of the $C_{11}$ substituent.

Any reference cited herein, including patents, patent applications, and publications, are hereby incorporate in their entireties by reference. Further, any reference herein to a component in the singular is intended to indicate and include at least one of that particular component, i.e., one or more.

While this invention has been described with an emphasis upon preferred embodiments, it will be obvious to those of ordinary skill in the art that variations of the perred embodiments, may be used and that it is intended that the invention may be practiced otherwise than as specifically described herein. Accordingly, this invention includes all modifications encompassed within the spirit and scope of the invention as defined by the following claims.

We claim as our invention:

1. A method for providing hormonal therapy to a patient comprising the oral administration of an androgen selected from the group consisting of 7α,11β-dimethyl-17βhydroxyestra-4,14-dien-3-one, 17-ester of 7α,11β-dimethyl-17β-hydroxyestra-4,14-dien-3-one, or mixtures thereof in an amount effective to provide hormonal therapy to a patient in need thereof, wherein the hormonal therapy is selected from the group consisting of hormone replacement therapy in males and females, male contraception, treatment of breast cancer, promotion and maintenance of muscle mass in a patient, treatment of osteoporosis, treatment of anemia, treatment for anabolic support, and hypergonadotropic conditions.

2. The method of claim 1, wherein an average dosage of about 1 mg to about 50 mg per day of the androgen is orally administered to the patient.

3. The method of claim 2, wherein the androgen is 7α,11β-dimethyl-17β-hydroxyestra-4,14-dien-3-one.

4. The method of claim 1, wherein the androgen is a 17-ester of 7α,11β-dimethyl-17β-hydroxyestra-4,14-dien-3-one.

5. The method of claim 4, wherein the androgen is 7α,11β-dimethyl-17βhydroxyestra-4,14-dien-3-one 17β-4-trans-n-butylcyclohexanecarboxylate.

6. The method of claim 5, wherein an average dosage of about 5 mg to about 40 mg per day of the androgen is orally administered to the patient.

7. The method of claim 4, wherein the androgen is 7α,11β-dimethyl-17β-hydroxyestra-4,14-dien-3-one 17-undecanoate.

8. The method of claim 7, wherein an average dosage of about 5 mg to about 40 mg per day of the androgen is orally administered to the patient.

9. The method of claim 2, wherein the oral administration is completed on a daily basis for at least one month.

10. The method of claim 9, wherein the hormonal therapy continues at least 3 months.

11. The method of claim 1, wherein the hormonal therapy is the treatment of hypogonadism in a male patient.

12. The method of claim 11, wherein an average dosage of about 1 mg to about 50 mg per day of the androgen is orally administered to the patient.

13. The method of claim 12, wherein the androgen is 7α,11β-dimethyl-17β-hydroxyestra-4,14-dien-3-one.

14. The method of claim 11, wherein the androgen is a 17-ester of 7α,11β-dimethyl-17β-hydroxyestra-4,14-dien-3-one.

15. The method of claim 14, wherein the androgen is 7α,11β-dimethyl-17β hydroxyestra-4,14-dien-3-one 17β-4-trans-n-butylcyclohexanecarboxylate.

16. The method of claim 15, wherein an average dosage of about 5 mg to about 40 mg per day of the androgen is orally administered to the patient.

17. The method of claim 14, wherein the androgen is 7α,11β-dimethyl-17β-hydroxyestra-4,14-dien-3-one 17-undecanoate.

18. The method of claim 17, wherein an average dosage of about 5 mg to about 40 mg per day of the androgen is orally administered to the patient.

19. The method of claim 12, wherein the oral administration is completed on a daily basis for at least one month.

20. The method of claim 19, wherein the hormonal therapy continues at least 3 months.

21. The method of claim 1, wherein the hormonal therapy is male contraception.

22. The method of claim 21, wherein an average dosage of about 1 mg to about 50 mg per day of the androgen is orally administered to the patient.

23. The method of claim 22, wherein the androgen is 7α,11β-dimethyl-17β-hydroxyestra-4,14-dien-3-one.

24. The method of claim 21, wherein the androgen is a 17-ester of 7α,11β-dimethyl-17β-hydroxyestra-4,14-dien-3-one.

25. The method of claim 24, wherein the androgen is 7α,11β-dimethyl-17β hydroxyestra-4,14-dien-3-one 17β-4-trans-n-butylcyclohexanecarboxylate.

26. The method of claim 25, wherein an average dosage of about 5 mg to about 40 mg per day of the androgen is orally administered to the patient.

27. The method of claim 24, wherein the androgen is 7α,11β-dimethyl-17β-hydroxyestra-4,14-dien-3-one 17-undecanoate.

28. The method of claim 27, wherein an average dosage of about 5 mg to about 40 mg per day of the androgen is orally administered to the patient.

29. The method of claim 22, wherein the oral administration is completed on a daily basis for at least one month.

30. The method of claim 29, wherein the hormonal therapy continues at least 3 months.

31. The method of claim 1, wherein the hormonal therapy is the promotion and maintenance of muscle mass in a patient.

32. The method of claim 31, wherein the therapy continues for at least 3 months.

33. The method of claim 31, wherein the androgen is 7α,11β-dimethyl-17β-hydroxyestra-4,14-dien-3-one.

34. The method of claim 31, wherein the androgen is a 17-ester of 7α,11β-dimethyl-17β-hydroxyestra-4,14-dien-3-one.

35. The method of claim 34, wherein the androgen is 7α,11β-dimethyl-17β hydroxyestra-4,14-dien-3-one 17β-4-trans-n-butylcyclohexanecarboxylate.

36. The method of claim 34, wherein the androgen is 7α,11β-dimethyl-17β-hydroxyestra-4,14-dien-3-one 17-undecanoate.

37. The method of claim 1, wherein the hormonal therapy is the pilliative treatment of breast cancer.

38. The method of claim 37, wherein the therapy continues for at least 3 months.

39. The method of claim 37, wherein the androgen is 7α,11β-dimethyl-17β-hydroxyestra-4,14-dien-3-one.

40. The method of claim 37, wherein the androgen is a 17-ester of 7α,11β-dimethyl-17β-hydroxyestra-4,14-dien-3-one.

41. The method of claim 40, wherein the androgen is 7α,11β-dimethyl-17β hydroxyestra-4,14-dien-3-one 17β-4-trans-n-butylcyclohexanecarboxylate.

42. The method of claim 40, wherein the androgen is 7α,11β-dimethyl-17β-hydroxyestra-4,14-dien-3-one 17-undecanoate.

43. The method of claim 1, wherein the hormonal therapy is hormone replacement therapy in females.

44. The method of claim 43, further comprising the administration of estrogen.

45. The method of claim 44, further comprising the administration of a progestin.

46. The method of claim 44, wherein the androgen is 7α,11β-dimethyl-17β-hydroxyestra-4,14-dien-3-one.

47. The method of claim 44, wherein the androgen is a 17-ester of 7α,11β-dimethyl-17β-hydroxyestra-4,14-dien-3-one.

48. The method of claim 47, wherein the androgen is 7α,11β-dimethyl-17β hydroxyestra-4,14-dien-3-one 17β-4-trans-n-butylcyclohexanecarboxylate.

49. The method of claim 47, wherein the androgen is 7α,11β-dimethyl-17β-hydroxyestra-4,14-dien-3-one 17-undecanoate.

50. The method of claim 1, wherein the androgen is administered as a formulation comprising the androgen and a pharmaceutically-acceptable oily carrier.

51. A method for providing hormonal therapy to a patient comprising administering parenterally to the patient an androgen selected from the group consisting of 7α,11β-dimethyl-17β-hydroxyestra-4,14-dien-3-one, a 17-ester of 7α,11β-dimethyl-17β-hydroxyestra-4,14-dien-3-one, and mixtures thereof in an amount effective to provide hormonal therapy to the patient, wherein the hormonal therapy is selected from the group consisting of hormone replacement therapy in males and females, male contraception, treatment of breast cancer, promotion and maintenance of muscle mass in a patient, treatment of osteoporosis, treatment of anemia, treatment for anabolic support, and hypergonadotropic conditions.

52. The method of claim 51, wherein an average dosage of about 1 to about 400 mg of the androgen is parenterally administered to the patient.

53. The method of claim 52, wherein the androgen is administered to the patient about once every month.

54. The method of claim 53, wherein the androgen is a 17-ester of 7α,11β-dimethyl-17β-hydroxyestra-4,14-dien-3-one.

55. The method of claim 51, wherein the androgen is administered to the patient about once every two to four months.

56. The method of claim 55, wherein the androgen is a 17-ester of 7α,11β-dimethyl-17β-hydroxyestra-4,14-dien-3-one.

57. The method of claim 56, wherein an average dosage of about 1 to about 400 mg of the androgen is parenterally administered to the patient.

58. The method of claim 54, wherein the androgen is 7α,11β-dimethyl-17β hydroxyestra-4,14-dien-3-one 17β-4-trans-n-butylcyclohexanecarboxylate.

59. The method of claim 54, wherein the androgen is 7α,11β-dimethyl-17β-hydroxyestra-4,14-dien-3-one 17-undecanoate.

60. The method of claim 51, wherein the average amount of the androgen administered during the period of hormonal therapy is from about 1 to about 40 mg per week.

61. The method of claim 51, wherein the androgen is 7α,11β-dimethyl-17β hydroxyestra-4,14-dien-3-one 17β-4-trans-n-butylcyclohexanecarboxylate and is administered as a formulation comprising 7α,11β-dimethyl-17β hydroxyestra-4,14-dien-3-one 17β-4-trans-n-butylcyclohexanecarboxylate and a pharmaceutically-acceptable aqueous carrier.

62. The method of claim 61, wherein the 7α,11β-dimethyl-17β hydroxyestra-4,14-dien-3-one 17β-4-trans-n-butylcyclohexanecarboxylate is crystalline and the formulation comprises a suspension of 7α,11β-dimethyl-17β hydroxyestra-4,14-dien-3-one 17β-4-trans-n-butylcyclohexanecarboxylate in the pharmaceutically-acceptable aqueous carrier.

63. The method of claim 62, wherein the formulation is administered about once every month.

64. The method of claim 62, wherein the formulation is administered about once every two to four months.

65. The method of claim 64, wherein from about 100 mg to about 400 mg of the androgen is administered to the patient.

66. The method of claim 51, wherein the androgen is 7α,11β-dimethyl-17β-hydroxyestra-4,14-dien-3-one and is administered as a formulation comprising 7α,11β-dimethyl-17β-hydroxyestra-4,14-dien-3-one and a pharmaceutically-acceptable aqueous carrier.

67. The method of claim 66, wherein the 7α,11β-dimethyl-17β-hydroxyestra-4,14-dien-3-one is crystalline and the formulation comprises a suspension of 7α,11β-dimethyl-17β-hydroxyestra-4,14-dien-3-one in the pharmaceutically-acceptable aqueous carrier.

68. The method of claim 67, wherein the formulation is administered about once every month.

69. The method of claim 67, wherein the formulation is administered about once every two to four months.

70. The method of claim 69, wherein from about 100 mg to about 400 mg of the androgen is administered to the patient.

71. The method of claim 51, wherein the hormonal treatment is the treatment of hypogonadism in male patients.

72. The method of claim 71, wherein an average dosage of about 1 to about 400 mg of the androgen is parenterally administered to the patient.

73. The method of claim 72, wherein the androgen is administered to the patient about once every month.

74. The method of claim 71, wherein the androgen is a 17-ester of 7α,11β-dimethyl-17β-hydroxyestra-4,14-dien-3-one.

75. The method of claim 71, wherein the androgen is administered to the patient about once every two to four months.

76. The method of claim 75, wherein an average dosage of about 1 to about 400 mg of the androgen is parenterally administered to the patient.

77. The method of claim 74, wherein the androgen is 7α,11β-dimethyl-17β hydroxyestra-4,14-dien-3-one 17β-4-trans-n-butylcyclohexanecarboxylate.

78. The method of claim 74, wherein the androgen is 7α,11β-dimethyl-17β-hydroxyestra-4,14-dien-3-one 17-undecanoate.

79. The method of claim 71, wherein the average amount of the androgen administered during the period of hormonal therapy is from about 1 to about 40 mg per week.

80. The method of claim 71, wherein the androgen is 7α,11β-dimethyl-17β hydroxyestra-4,14-dien-3-one 17β-4-trans-n-butylcyclohexanecarboxylate and is administered as a formulation comprising 7α,11β-dimethyl-17β hydroxyestra-4,14-dien-3-one 17β-4-trans-n-butylcyclohexanecarboxylate and a pharmaceutically-acceptable aqueous carrier.

81. The method of claim 80, wherein the 7α,11β-dimethyl-17β hydroxyestra-4,14-dien-3-one 17β-4-trans-n-butylcyclohexanecarboxylate is crystalline and the formulation comprises a suspension of 7α,11β-dimethyl-17β hydroxyestra-4,14-dien-3-one 17β-4-trans-n-butylcyclohexanecarboxylate in the pharmaceutically-acceptable aqueous carrier.

82. The method of claim 81, wherein the formulation is administered about once every month.

83. The method of claim 81, wherein the formulation is administered about once every two to four months.

84. The method of claim 81, wherein from about 100 mg to about 400 mg of the androgen is administered to the patient.

85. The method of claim 51, wherein the hormonal treatment is male contraception.

86. The method of claim 85, wherein an average dosage of about 1 to about 400 mg of the androgen is parenterally administered to the patient.

87. The method of claim 86, wherein the androgen is administered to the patient about once every month.

88. The method of claim 85, wherein the androgen is a 17-ester of 7α,11β-dimethyl-17β-hydroxyestra-4,14-dien-3-one.

89. The method of claim 85, wherein the androgen is administered to the patient about once every two to four months.

90. The method of claim 88, wherein an average dosage of about 1 to about 400 mg of the androgen is parenterally administered to the patient.

91. The method of claim 88, wherein the androgen is 7α,11β-dimethyl-17β hydroxyestra-4,14-dien-3-one 17β-4-trans-n-butylcyclohexanecarboxylate.

92. The method of claim 88, wherein the androgen is 7α,11β-dimethyl-17β-hydroxyestra-4,14-dien-3-one 17-undecanoate.

93. The method of claim 85, wherein the average amount of the androgen administered during the period of hormonal therapy is from about 1 to about 40 mg per week.

94. The method of claim 85, wherein the androgen is 7α,11β-dimethyl-17β hydroxyestra-4,14-dien-3-one 17β-4-trans-n-butylcyclohexanecarboxylate and is administered as a formulation comprising 7α,11β-dimethyl-17β hydroxyestra-4,14-dien-3-one 17β-4-trans-n-butylcyclohexanecarboxylate and a pharmaceutically-acceptable aqueous carrier.

95. The method of claim 85, wherein the androgen is 7α,11β-dimethyl-17β-hydroxyestra-4,14-dien-3-one and is administered as a formulation comprising 7α,11β-dimethyl-17β-hydroxyestra-4,14-dien-3-one and a pharmaceutically-acceptable aqueous carrier.

96. The method of claim 93, wherein the androgen is a 17-ester of 7α,11β-dimethyl-17β-hydroxyestra-4,14-dien-3-one.

* * * * *

UNITED STATES PATENT AND TRADEMARK OFFICE
CERTIFICATE OF CORRECTION

PATENT NO. : 7,196,074 B2
APPLICATION NO. : 10/281794
DATED : March 27, 2007
INVENTOR(S) : Blye et al.

It is certified that error appears in the above-identified patent and that said Letters Patent is hereby corrected as shown below:

IN THE TITLE PAGE:

Item (73) Assignee: "The United States of America as represented by the Department of Health and Human Services, Washington, DC (US)"

should read --Government of the United States of America, represented by the Secretary, Department of Health and Human Services, Rockville, Maryland--.

IN THE CLAIMS

Column 32, Line 28 Claim 1: "17βhydrox-" should read -- 17β-hydrox- --.

Signed and Sealed this

Fifth Day of June, 2007

JON W. DUDAS
*Director of the United States Patent and Trademark Office*